(12) United States Patent
Konno et al.

(10) Patent No.: US 6,958,353 B2
(45) Date of Patent: Oct. 25, 2005

(54) IMIDAZOLE DERIVATIVES OR SALTS THEREOF AND DRUGS CONTAINING THE DERIVATIVES OR THE SALTS

(75) Inventors: Fujiko Konno, Chiba (JP); Yoshihiro Nagao, Chiba (JP); Kazuo Isomae, Chiba (JP); Mari Ohtsuka, Chiba (JP); Yoshiyuki Takahashi, Chiba (JP); Fumio Ishii, Miyagi (JP); Hiroyuki Hirota, Chiba (JP); Sunao Takeda, Chiba (JP); Noriyuki Kawamoto, Chiba (JP); Haruyoshi Honda, Chiba (JP); Susumu Sato, Chiba (JP)

(73) Assignee: Hisamitsu Medical Co., Ltd., Tokyo (JP)

( * ) Notice: Subject to any disclaimer, the term of this patent is extended or adjusted under 35 U.S.C. 154(b) by 121 days.

(21) Appl. No.: 10/258,610

(22) PCT Filed: Jun. 8, 2001

(86) PCT No.: PCT/JP01/04836

§ 371 (c)(1),
(2), (4) Date: Nov. 5, 2002

(87) PCT Pub. No.: WO02/00648

PCT Pub. Date: Jan. 3, 2002

(65) Prior Publication Data

US 2003/0207896 A1 Nov. 6, 2003

(30) Foreign Application Priority Data

Jun. 28, 2000 (JP) .................................. 2000-194024

(51) Int. Cl.[7] .................. C07D 233/60; C07D 401/14; A61K 31/4178; A61K 31/444; A61P 19/02
(52) U.S. Cl. .................. 514/336; 546/272.7; 544/405; 514/255.05
(58) Field of Search .................. 546/272.7; 514/336

(56) References Cited

U.S. PATENT DOCUMENTS 4,755,526 A 7/1988 Hirsch et al.

5,888,999 A 3/1999 Bodick et al.

FOREIGN PATENT DOCUMENTS

| DE | 195 41 146 | 4/1997 |
| EP | 0 293 978 | 12/1988 |
| EP | 0 757 988 | 2/1997 |
| JP | 7-33752 | 2/1995 |
| JP | 7-126256 | 5/1995 |
| JP | 11-158156 | 6/1999 |
| WO | WO 94/12461 | 6/1994 |
| WO | WO 99/17777 | 4/1999 |
| WO | WO 01/34578 | * 5/2001 |

OTHER PUBLICATIONS

Fons et al. Cytokine ((7) 453–462, 1997.*

* cited by examiner

Primary Examiner—Venkataraman Balasubramanian
(74) Attorney, Agent, or Firm—Oblon, Spivak, McClelland, Maier & Neustadt, P.C.

(57) ABSTRACT

The invention is directed to an imidazole derivative represented by formula (1):

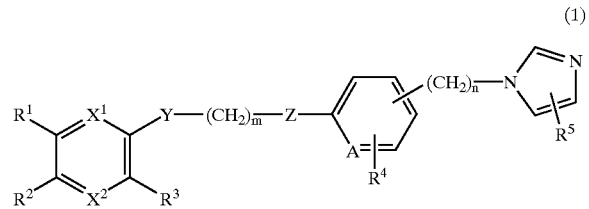

wherein each of $R^1$ and $R^2$ represents an aryl group, a heteroaryl group, etc.; each of A, $X^1$, and $X^2$ represents N or CH; each of Y and Z represents O, S, etc.; each of $R^3$, $R^4$, and $R^5$ represents a hydrogen atom, an alkyl group, etc.; m is a number of 1 to 4; and n is a number of 0 to 4, or a salt thereof. The invention is also directed to a drug containing the derivative or the salt as an active ingredient. These compounds exert excellent effects of inhibiting production of NO and IL-6 and are useful for preventing or treating diseases induced by overproduction of NO and IL-6.

20 Claims, 1 Drawing Sheet

IMIDAZOLE DERIVATIVES OR SALTS THEREOF AND DRUGS CONTAINING THE DERIVATIVES OR THE SALTS

TECHNICAL FIELD

The present invention relates to a novel imidazole derivative or a salt thereof and to a drug containing the derivative or the salt as an active ingredient.

BACKGROUND ART

Nitric oxide (NO) synthesized in living organisms by the mediation of a nitric oxide synthase (NOS) is considered to be involved in a variety of biological reaction steps.

Forchgott et al. disclose that endothelium-derived relaxing factors (EDRFs) exert strong angiectatic effect and platelet aggregation inhibitory effect (1980). Palmer et al. disclose that the EDRFs essentially are in fact NO (1987). Further studies have revealed that NO is produced in vascular endothelial cells as well as in a variety of tissue cells in the whole body; e.g., the cerebellum, platelets, peripheral nerves, macrophages, polynuclear leucocytes, hepatocytes, Kupffer's cells, kidney mesangial cells, lung parenchyma cells, adrenal vascular smooth muscle, and fibroblasts. In addition to the previously identified effect of relaxing vascular smooth muscle, NO has now been elucidated to function as a neurotransmitter and exert various effects such as a cytotoxic effect on bacteria and oncocytes.

It has also been reported that when NO is overproduced and released in the body, a variety of cells and tissues are damaged because of high reactivity of NO stemming from its chemical instability and NO's effect of relaxing vascular smooth muscle. Particularly, in recent years, the relationship between inflammatory diseases and NO released from activated leucocytes has become of interest. Thus, a drug which inhibits production of NO is envisaged to exert an anti-inflammatory effect.

Meanwhile, interleukin 6 (IL-6) is known to be produced from cells such as monocytes, T cells, B cells, vascular endothelial cells, fibroblasts, and osteoblasts, and to exert a variety of physiological effects including induction effects of differentiating B cells into antibody-producing cells; for synthesizing acute phase protein from hepatocytes; for differentiating cerebral nerve cells; for proliferating and differentiating hematopoietic cells; and for differentiating osteoclasts. In addition, the relationship between IL-6 and inflammation has become of interest.

Chronic rheumatoid arthritis is a type of systemic chronic inflammatory disease in which the joints exhibit anomalous proliferation of connective tissue such as synovial tissue. As has been reported, an excessive amount of IL-6 is present in the serum or synovial fluid of chronic rheumatoid arthritis patients, and proliferation of synovial cells can be suppressed through administration of an antagonist for inhibiting IL-6 activity, such as an IL-6 antibody or an IL-6 receptor.

Among known physiological effects of IL-6, the aforementioned induction effect of differentiating osteoblasts is considered to be a factor responsible for the onset of osteoporosis resulting from bone hyper-resorption of osteoblasts. Accordingly, a drug which inhibits overproduction of IL-6 is envisaged to be effective for chronic inflammatory diseases such as chronic rheumatoid arthritis and for osteoporosis.

Thus, an object of the present invention is to provide a novel compound useful for preventing or treating a disease induced by overproduction of NO or IL-6.

DISCLOSURE OF THE INVENTION

The present inventors have synthesized a variety of compounds and carried out extensive studies on pharmacological effects of the compounds, and have found that imidazole derivatives or salts thereof represented by the below-mentioned formula (1) exert excellent effects of inhibiting production of NO and IL-6 and are useful for preventing or treating diseases induced by overproduction of NO and IL-6. The inventors have also found that these derivatives and salts exert an effect of inhibiting production of prostaglandin $E_2$ ($PGE_2$) but no ulcer-inducing effect, which is an adverse side effect of non-steroidal anti-inflammatory drugs such as indomethacin. The present invention has been accomplished on the basis of these findings.

Accordingly, the present invention provides an imidazole derivative represented by formula (1):

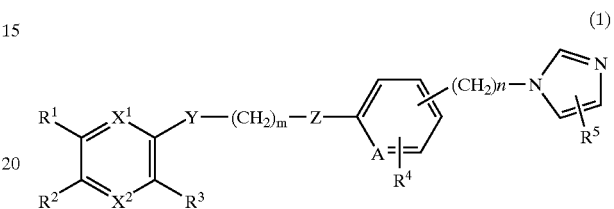

wherein each of $R^1$ and $R^2$ represents a hydrogen atom, an alkyl group, a halogen atom, an aryl group which may be substituted, or a heteroaryl group which may be substituted;

each of A, $X^1$, and $X^2$ represents N or CH;

each of Y and Z represents O, S, SO, $SO_2$, $CH_2$, NH, or N—$R^6$ (wherein $R^6$ represents an alkyl group, an aryl group which may be substituted, or a heteroaryl group which may be substituted);

each of $R^3$, $R^4$, and $R^5$ represents a hydrogen atom, an alkyl group, an alkoxy group, a halogen atom, a halogenoalkyl group, a nitro group, an amino group, a hydroxyl group, a cyano group, an acyl group, a carboxyl group, a carbamoyl group, a substituted amide group, a substituted sulfonamido group or a phenyl group which may be substituted;

m is a number of 1 to 4; and n is a number of 0 to 4, or a salt thereof.

The present invention also provides a drug comprising, as an active ingredient, the aforementioned imidazole derivative (1) or the salt thereof.

The present invention also provides a drug composition comprising the aforementioned imidazole derivative (1) or the salt thereof and a pharmaceutically acceptable carrier.

The present invention further provides use of the aforementioned imidazole derivative (1) or the salt thereof for producing a drug.

The present invention further provides a method for treating a disease induced by overproduction of NO or IL-6 characterized by comprising administrating the aforementioned imidazole derivative (1) or the salt thereof.

BEST MODES FOR CARRYING OUT THE INVENTION

Figure 1:
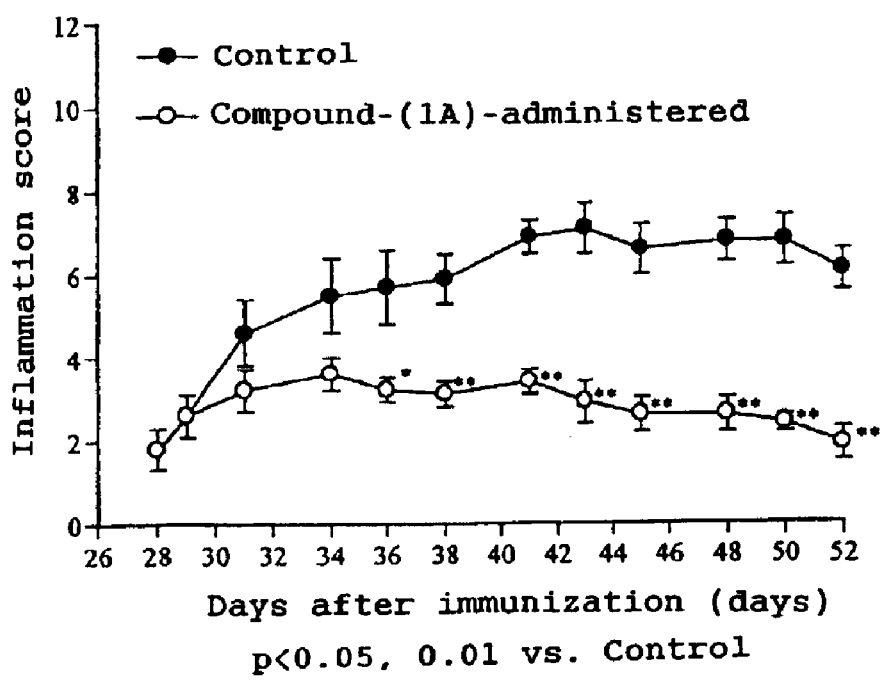
FIG. 1 is a graph showing changes in inflammation score observed in Test Example 3.

The compounds according to the present invention are represented by the aforementioned formula (1). Examples of the alkyl groups represented by $R^1$, $R^2$, $R^3$, $R^4$, $R^5$, or $R^6$, include C1–C6, linear or branched alkyl groups. Specific examples include methyl, ethyl, n-propyl, isopropyl, n-butyl, isobutyl, tert-butyl, pentyl, and hexyl. Of these, methyl and ethyl are particularly preferred.

Examples of the halogen atoms represented by $R^1$, $R^2$, $R^3$, $R^4$, or $R^5$ include a fluorine atom, a chlorine atom, and a bromine atom. Of these, a chlorine atom is particularly preferred.

Examples of the alkoxy groups represented by $R^3$, $R^4$, or $R^5$ include C1–C6 linear or branched alkoxy groups. Specific examples include methoxy, ethoxy, propoxy, isopropoxy, butoxy, pentyloxy, and hexyloxy. Of these, methoxy and ethoxy are particularly preferred.

Examples of the halogenoalkyl groups represented by $R^3$, $R^4$, or $R^5$ include C1–C6 linear or branched halogenoalkyl groups. Of these, those of C1–C3 are preferred, with a trifluoromethyl group being particularly preferred.

Examples of the acyl groups represented by $R^3$, $R^4$, or $R^5$ include alkanoyl groups such as C1–C6 alkanoyl groups. Specific examples include formyl, acetyl, and propionyl.

Examples of the aryl groups represented by $R^1$, $R^2$, $R^3$, $R^4$, $R^5$, or $R^6$ include C6–C14 aryl groups. Specific examples include phenyl, naphthyl, and anthranyl. Of these, phenyl and naphthyl are particularly preferred. Examples of the heteroaryl groups include 5- or 6-membered heteroaryl groups having one or two nitrogen, sulfur, or oxygen atoms. Specific examples include pyrrolyl, furyl, thienyl, imidazolyl, pyridyl, and pyrazinyl. Of these, thienyl, imidazolyl, pyridyl, and pyrazinyl are particularly preferred.

Examples of the groups which can serve as a substituent for the aryl group or heteroaryl group represented by $R^1$ or $R^2$ include one to three groups selected from among halogen atoms, a nitro group, amino groups, alkyl groups, a hydroxy group, alkoxy groups, alkylthio groups, alkylsulfonyl groups, alkylenedioxy groups, and halogenoalkyl groups. Examples of the groups which can serve as a substituent for the aryl group or heteroaryl group represented by $R^6$ include alkyl groups, alkoxy groups, amino groups, and sulfonamide groups. Examples of the groups which can serve as a substituent for phenyl group represented by $R^3$, $R^4$, or $R^5$ include alkyl groups, alkoxy groups, amino groups, and sulfonamide groups. Examples of the groups which can serve as a substituent for the amide or sulfonamide group represented by $R^3$, $R^4$, or $R^5$ include alkyl groups. Specifically, an alkanoylamino group is a preferred substituted amide group, and an alkanesulfonamide group is a preferred substituted-sulfonamide group. Examples of the alkyl groups, alkoxy groups, halogen atoms, and halogenoalkyl groups which can serve as a substituent for these aryl groups or heteroaryl groups include the same groups as described in relation to the aforementioned $R^1$ to $R^6$. Examples of the alkylthio groups include C1–C6 linear or branched alkylthio groups. Specific examples include methylthio and ethylthio. Examples of the alkylsulfonyl groups include C1–C6 linear or branched alkylsulfonyl groups. Specific examples include methylsulfonyl and ethylsulfonyl. Examples of the alkylenedioxy groups include C1 or C2 alkylenedioxy groups. Of these, methylenedioxy are is preferred.

Examples of the groups represented by $R^1$ or $R^2$ of formula (1) include a hydrogen atom; halogen atoms; C1–C6 alkyl groups; a phenyl or naphthyl group which may be substituted by one to three substituents selected from among a halogen atom, a nitro group, an amino group, a C1–C6 alkyl group, a hydroxyl group, a C1–C6 alkoxy group, a C1–C6 alkylthio group, a C1–C6 alkylsulfonyl group, a C1–C2 alkylenedioxy group, and a C1–C6 halogenoalkyl group; and a pyridyl, imidazolyl, pyrazinyl, or thienyl group which may be substituted by one to three substituents selected from among a halogen atom, a nitro group, an amino group, a C1–C6 alkyl group, a hydroxyl group, a C1–C6 alkoxy group, a C1–C6 alkoxy group, a C1–C6 alkylthio group, a C1–C6 alkylsulfonyl group, a C1–C2 alkylenedioxy group, and a C1–C6 halogenoalkyl group. Examples of preferred groups represented by Y or Z include O, $CH_2$, NH, and N—$R^6$ ($R^6$=C1–C6 alkyl). Of these, O and $CH_2$ are particularly preferred. Examples of preferred groups represented by $R^3$, $R^4$, or $R^5$ include a hydrogen atom, a halogen atom, a nitro group, an amino group, a C1–C6 alkyl group, and a C1–C6 alkoxy group. m preferably falls within 1 to 3. n preferably falls within 0 to 2.

No particular limitation is imposed on the species of the salt of the imidazole derivative (1) of the present invention, and any of these salts may be used so long as the salts are pharmaceutically acceptable. Examples of the preferred salts include hydrogen halide salts such as hydrofluorides, hydrochlorides, hydrobromides, and hydroiodides; inorganic salts such as carbonates, nitrates, perchlorates, sulfates, and phosphates; lower-alkysulfonates such as methanesulfonates, ethanesulfonates, and trifluoromethanesulfonates; arylsulfonates such as benzenesulfonates and p-toluenesulfonates; organic acid salts such as fumarates, maleates, succinates, citrates, tartrates, and oxalates; aminoacid salts such as glutamates and aspartates; and salts of an alkali metal or alkaline earth metal such as sodium, potassium, or calcium.

In addition, hydrates, a variety of pharmaceutically acceptable solvates, crystal polymorphisms, etc. of the compounds represented by formula (1) also fall within the scope of the present invention. Stereoisomers attributed to asymmetric carbon are also included.

The imidazole derivatives (1) of the present invention may be produced through the following production methods 1 to 5.

<Production method 1>

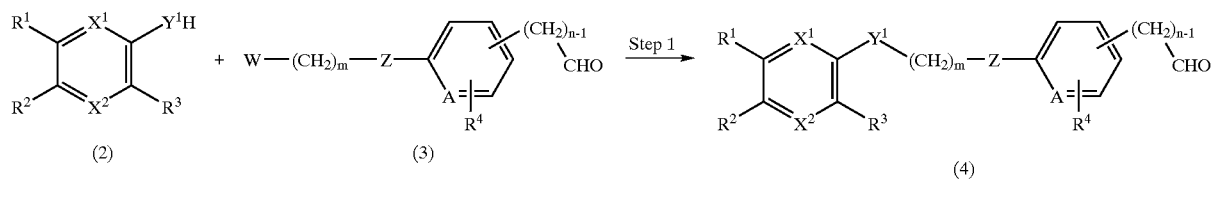

(2)   (3)   (4)

Step 2

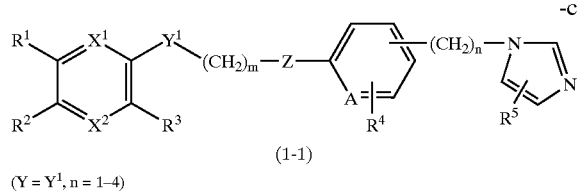
(1-1)

(Y = Y¹, n = 1–4)

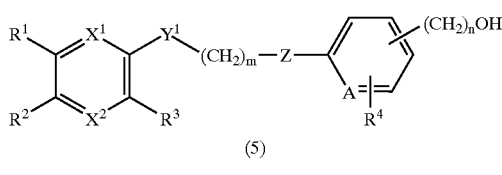
(5)

Step 3

($R^1$, $R^2$, $X^1$, $X^2$, A, Z, $R^3$, $R^4$, $R^5$, and m represent the same as defined above; $Y^1$ represents O, S, NH, or N—$R^6$ ($R^6$ represents the same as defined above); n is a number of 1 to 4; W represents a leaving group).

Specifically, Compound (1-1) of the present invention represented by formula (1) (wherein Y is O, S, NH, or N—$R^6$, and n is 1 to 4) may be produced in the following manner. Compound (2) is reacted with Compound (3), to thereby form Compound (4) (Step 1). The aldehyde moiety of the thus-formed Compound (4) is reduced to the corresponding alcohol moiety by use of a reducing agent, to thereby form Compound (5) (Step 2). The Compound (5) is reacted with a halogenating agent, followed by reaction with an imidazole derivative (Step 3). Each step will next be described in detail.

(Step 1)

Compound (2) is reacted with an aldehyde derivative (3) having a terminal leaving group in the presence of an appropriate base and solvent, to thereby yield Compound (4).

Compound (2), serving as a starting material, is prepared through any of known methods (e.g., disclosed in J. Am. Chem. Soc., 74, 1580 (1952); J. Am. Chem. Soc., 107, 972 (1985); J. Org. Chem., 57, 550 (1992); J. Org. Chem., 28, 3468 (1963); J. Org. Chem., 60, 1408 (1995); and Japanese Patent Application Laid-Open (kokai) No. 7-33752). Any commercial reagent of Compound (3) may be used. Alternatively, Compound (3) may be produced through halogenation or sulfonylation of a terminal hydroxyl group of an aldehyde derivative synthesized through a known method (e.g., disclosed in Journal of Heterocyclic Chemistry, 6, 243 (1969) and Japanese Patent Application Laid-Open (kokai) No. 8-92228). Examples of the leaving group W include halogen atoms such as chlorine, bromine, and iodine; a methanesulfonyloxy group; a p-toluenesulfonyloxy group; and a trifluoromethanesulfonyloxy group. Of these, a methanesulfonyloxy group is preferred.

Examples of the base employed in the reaction of Compound (2) with Compound (3) include sodium hydride, calcium hydride, potassium t-butoxide, sodium hydroxide, potassium hydroxide, and potassium carbonate. No particular limitation is imposed on the type of solvent, and any solvent can be employed so long as the solvent does not affect the reaction. Examples of the solvents include ethers such as tetrahydrofuran and dioxane; hydrocarbons such as benzene and toluene; amides such as dimethylformamide, dimethylacetamide, and N-methyl-α-pyrrolidone; and sulfoxides such as dimethyl sulfoxide. The reaction is carried out under ice-cooling conditions or reflux conditions. Preferably, the reaction is preformed in dimethylformamide in the presence of potassium carbonate at 70 to 100° C. for about 2 to about 5 hours under stirring.

(Step 2)

Compound (4) is reduced by use of a reducing agent in the presence of a solvent, to thereby yield the corresponding alcohol form (5).

Examples of the solvent employed in the above reduction include lower alcohols such as methanol and ethanol; and ethers such as ethyl ether and tetrahydrofuran. Examples of the reducing agents include sodium borohydride, lithium borohydride, and aluminum lithium hydride. Of these, sodium borohydride is preferred. The reduction is preferably carried out under ice-cooling or at room temperature with stirring for 0.5 to 2 hours.

(Step 3)

The thus-formed alcohol form (5) is treated with a halogenating agent in the presence or absence of solvent, to thereby form the corresponding halide, and the halide is reacted with an imidazole derivative, to thereby yield Compound (1-1) of the present invention.

Preferably, the alcohol form (5) is reacted with thionyl chloride in methylene chloride in the presence of a catalytic amount of dimethylformamide, followed by removing the solvent through distillation under reduced pressure. The residue was dissolved in dimethylformamide, and an imidazole derivative is added to the solution. The mixture is allowed to react at 90–100° C. for 1 to 2 hours.

<Production method 2>

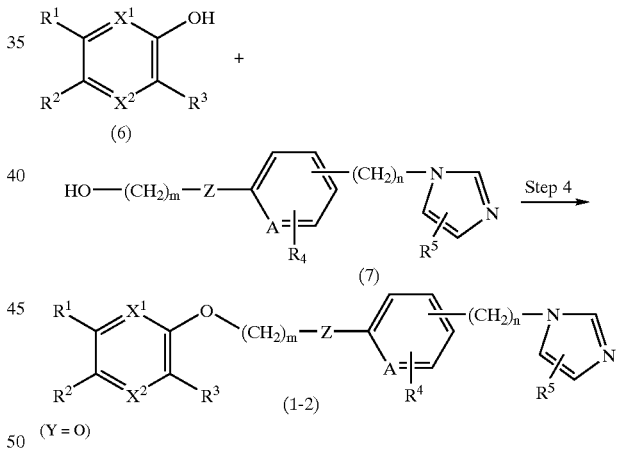

(Y = O)

($R^1$, $R^2$, $X^1$, $X^2$, A, Z, $R^3$, $R^4$, $R^5$, m, and n represent the same as defined above).

(Step 4)

Compound (1-2) of the present invention represented by formula (1) (wherein Y is O) may be produced through Mitsunobu reaction (Organic Reaction 42, 335) of Compound (6) with an imidazole derivative (7) having a terminal hydroxyl group.

Specifically, triphenyl phosphine (1-3 eq.) and dialkyl (e.g., dimethyl, diethyl, or dipropyl) azobiscarboxylate (1-3 eq.) are added to a solution of Compound (6) dissolved in a solvent (e.g., methylene chloride, tetrahydrofuran, benzene, toluene, ether, dioxane, or dimethylformamide), and the resultant mixture is allowed to react at −5° C. to reflux temperature for about 1 to about 24 hours, to thereby yield Compound (1-2) of the present invention.

<Production method 3>

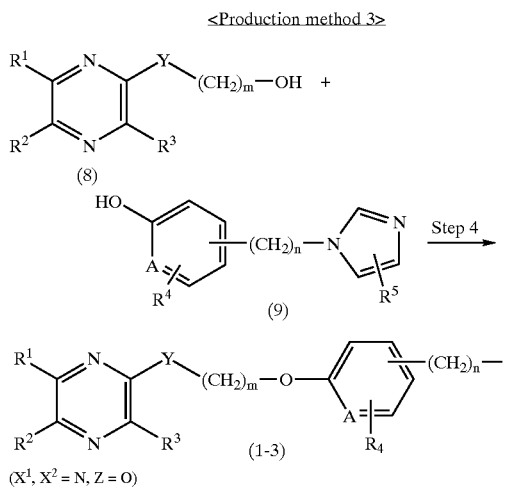

($X^1$, $X^2$ = N, Z = O)

($R^1$, $R^2$, A, Y, $R^3$, $R^4$, $R^5$, m, and n represent the same as defined above).

Compound (1-3) of the present invention represented by formula (1) (wherein each of $X^1$ and $X^2$ is N, and Z is O) may be produced in a manner similar to that employed in production method 2 (Step 4); i.e., through Mitsunobu reaction of a pyrazine derivative (8) having a terminal hydroxyl group with an imidazole derivative (9) having a phenolic hydroxyl group.

The pyrazine derivative (8), serving as a starting material, can be produced through any of known methods (e.g., methods disclosed in Japanese Patent Application Laid-Open (kokai) Nos. 7-33752 and 7-126256).

<Production method 4>

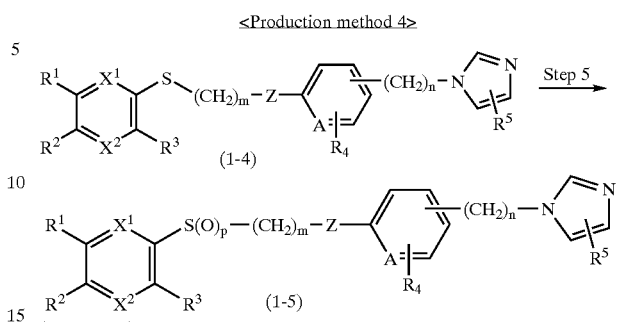

(Y = SO, $SO_2$)

($R^1$, $R^2$, $X^1$, $X^2$, A, Z, $R^3$, $R^4$, $R^5$, m, and n represent the same as defined above, and p represents 1 or 2).

(Step 5)

Compound (1-5) of the present invention represented by formula (1) (wherein Y is SO or $SO_2$) may be produced by treating, with an oxidizing agent, Compound (1-4) of the present invention produced through the aforementioned Production methods 1 to 3.

Examples of the oxidizing agent include peracetic acid, perbenzoic acid, m-chloroperbenzoic acid, and permaleic acid. Of these, m-chloroperbenzoic acid is particularly preferred. By modifying the amount of the employed oxidizing agent, compounds of p=1 or p=2 can be produced selectively.

<Production method 5>

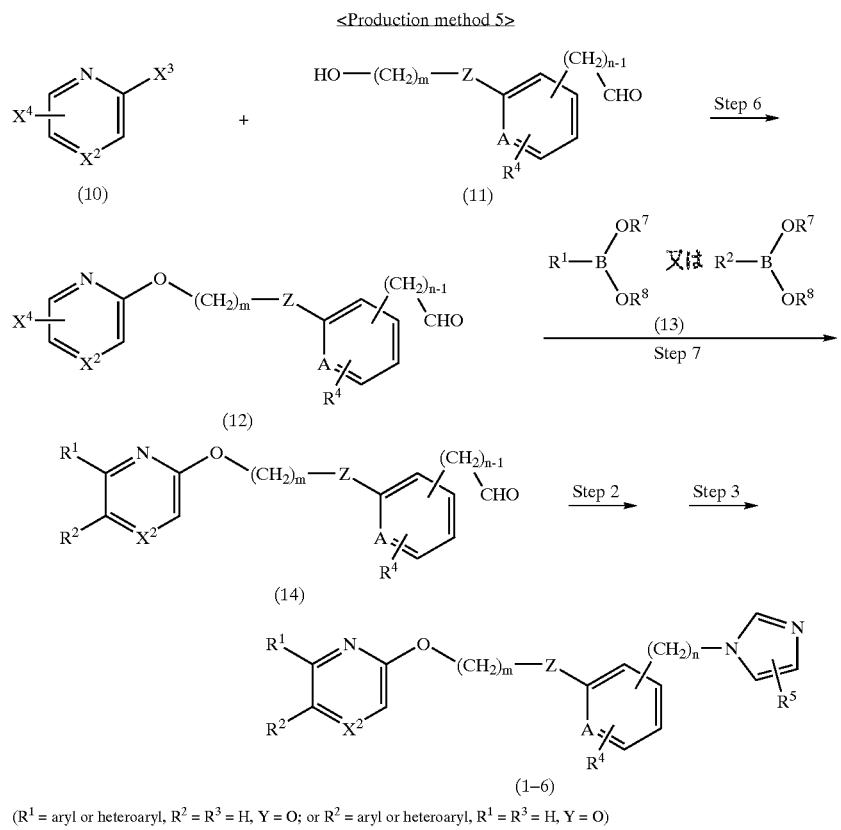

($R^1$ = aryl or heteroaryl, $R^2$ = $R^3$ = H, Y = O; or $R^2$ = aryl or heteroaryl, $R^1$ = $R^3$ = H, Y = O)

(each of $X^3$ and $X^4$ represents a halogen atom; each of $R^7$ and $R^8$ represents a hydrogen atom or a lower alkyl; $R^7$ and $R^8$ may be linked to form a ring; and A, $X^2$, $R^4$, $R^5$, Z, m, and n represent the same as defined above).

Specifically, Compound (10) is reacted with an aldehyde derivative (11), to thereby form Compound (12) (Step 6), followed by reaction with Compound (13), to thereby form Compound (14) (Step 7). The Compound (14) is reduced (Step 2), and the reduced product is reacted with a halogenating agent, followed by reaction with an imidazole derivative, to thereby yield Compound (1-6) of the present invention (Step 3).

(Step 6)

Compound (10) is reacted with an aldehyde derivative (11) in the presence of an appropriate base and solvent, to thereby yield Compound (12). Examples of the base employed in the reaction include sodium hydride, calcium hydride, potassium t-butoxide, sodium hydroxide, potassium hydroxide, and potassium carbonate. No particular limitation is imposed on the solvent employed in the reaction, and any solvent can be employed so long as the solvent does not affect the reaction. Examples of the solvent employed in the reaction include ethers such as tetrahydrofuran and dioxane; hydrocarbons such as benzene and toluene; amides such as dimethylformamide, dimethylacetamide, and N-methyl-α-pyrrolidone; sulfoxides such as dimethyl sulfoxide. The reaction is performed under ice-cooling or reflux conditions. Preferably, the reaction is performed in tetrahydrofuran in the presence of potassium t-butoxide at 70–100° C. for about 2 to about 5 hours under stirring.

(Step 7)

Compound (12) is-reacted with Compound (13) in the presence of an appropriate catalyst, base, and solvent, to thereby yield Compound (14).

Examples of the catalyst employed in the reaction include tetrakis(triphenylphosphine)palladium, tris(dibenzylidene acetone)dipalladium-tri(t-butylphosphine), palladium acetate-triphenylphosphine, and dichloro[1,1'-bis (diphenylphosphino)ferrocene]. Examples of the base employed in the reaction include sodium carbonate, sodium t-butoxide, sodium methoxide, cesium carbonate, sodium hydroxide, and potassium phosphate. Examples of the solvent employed in the reaction include toluene, benzene, xylene, tetrahydrofuran, and dioxane. The reaction is performed under reflux conditions. Preferably, the reaction is performed in benzene in the presence of tetrakis (triphenylphosphine)palladium and an aqueous solution of sodium carbonate at 100° C. for about 2 to about 20 hours under stirring.

The Compound (14) synthesized in Step 7 is subjected to the aforementioned Steps 2 and 3, to thereby produce Compound (1-6) of the present invention.

The thus-yielded Compounds (1) of the present invention can be isolated as crystal, liquid, or other forms through, in accordance with needs, a routine separation-purification method such as recrystallization, distillation, or chromatography.

The imidazole derivatives (1) of the present invention or salts thereof exert effect of inhibiting production of NO and IL-6, and therefore, are useful as drug for preventing or treating diseases induced by overproduction of NO or IL-6 (e.g., chronic inflammatory diseases such as chronic rheumatoid arthritis and osteoarthritis; shock (e.g., septic shock); ulcerative colitis; ischemic brain disorders; and osteoporosis); NO production suppressors; IL-6 production suppressors; etc.

The drug of the present invention may be formed into a variety of drug preparations in accordance with the pharmaceutical action and the target, object, and form of administration. Specifically, the imidazole derivative (1) or a salt thereof in an amount for effective for serving as an active component is mixed with a known pharmaceutically acceptable additive such as a vehicle, a binder, a disintegrant, a lubricant, a solution adjuvant, and a suspending agent, and the resultant mixture is formed into a preparation through a routine method.

Examples of the type of administration include peroral administration by way of tablets, capsules, granules, powders, syrups, etc.; and non-peroral administration by way of injections, eye drops, suppositories, etc. The amount of the imidazole derivative (1) to be administered varies in accordance with the condition, age, body weight of the patient, the way of administration, etc. Generally, the daily dose per adult is 0.1 to 1,000 mg and the drug is administered preferably once per day or several times per day in a divided manner.

The imidazole derivatives (1) of the present invention and salts thereof can be administered to human, and serve as veterinary drugs for other mammals.

EXAMPLES

The present invention will next be described in more detail by way of examples, which should not be construed as limiting the invention thereto.

Production Example 1

Synthesis of 4-(2-[(5,6-diphenyl-2-pyrazinyl)oxy] ethoxy)benzaldehyde

To a mixture containing 5,6-diphenyl-2-pyrazinol (2.45 g), 4-[2-(methanesulfonyloxy)ethoxy]benzaldehyde (2.44 g), and potassium carbonate (1.8 g), dimethylformamide (100 mL) was added. The resultant mixture was heated at 100° C. on an oil bath for two hours under stirring, and the reaction mixture was poured into an ice-water mixture. The thus-formed organic matter was separated through extraction by use of ethyl acetate, followed by washing sequentially with water and saturated saline. The washed product was dried over sodium sulfate anhydrate, and the residual solvent was removed through distillation under reduced pressure. The thus-yielded residue was purified by means of a silica gel column and crystallized from n-hexane, to thereby yield 3.34 g of the title compound (yield 85.4%).

$^1$H-NMR (CDCl$_3$, δ): 4.46(2H, t), 4.86(2H, t), 6.94–7.52 (12H, m), 7.71–7.88(2H, m), 8.32(1H, m), 9.90(1H, m).

Production Example 2

Synthesis of (4-(2-[(5,6-diphenyl-2-pyrazinyl)oxy] ethoxy)phenyl)methanol (4-(2-[(5,6-Diphenyl-2-pyrazinyl)oxy]ethoxy) benzaldehyde (2.90 g) was dissolved in ethanol (30 mL), and sodium borohydride (615 mg) was added to the resultant solution under ice cooling. The mixture was stirred at room temperature for one hour. Subsequently, water was added to the reaction mixture, and the thus-formed organic matter was separated through extraction by use of methylene chloride, followed by washing sequentially by water and saturated saline. The washed product was dried over sodium sulfate anhydrate, and the residual solvent was removed through distillation under reduced pressure. The thus-yielded residue was crystallized from n-hexane, to thereby yield 2.69 g of the title compound as colorless crystals (yield 92.3%).

$^1$H-NMR (CDCl$_3$, δ): 1.69(1H, t), 4.37(2H, t), 4.61(2H, d), 4.82(2H, t), 6.83–7.04(2H, m), 7.08–7.56(12H, m), 8.31 (1H, s).

Production Example 3

Synthesis of 4-{2-[(6-bromo-2-pyridinyl)oxy]ethoxy}benzaldehyde

To a 60% suspension of sodium hydride (0.22 g) in DMF (30 mL), 4-(2-hydroxyethoxy)benzaldehyde (1.00 g) was added at 0° C., and the suspension was stirred for 30 minutes. Subsequently, 2,6-dibromopyridine (2.14 g) and tetrabutylammonium iodide (0.022 g) were sequentially added to the mixture at 0° C., and the resultant mixture was stirred at room temperature for two hours. After completion of reaction, the reaction mixture was poured into an ice-water mixture, and the thus-formed organic matter was separated through extraction by use of ethyl acetate, followed by washing with water. The washed product was dried over magnesium sulfate, and the residual solvent was removed through distillation under reduced pressure. The thus-yielded residue was purified by means of a silica gel column, to thereby yield 1.50 g of the title compound as colorless crystals (yield 77.3%).

$^1$H-NMR (CDCl$_3$, δ): 4.40(2H, t, J=4.9 Hz), 4.71(2H, t, J=4.9 Hz), 6.75(1H, d, J=7.8 Hz), 7.07(2H, d, J=8.8 Hz), 7.10(1H, d, J=7.8 Hz), 7.45(1H, t, J=7.8 Hz), 7.85(2H, d, J=8.8 Hz), 9.90(1H, s).

Production Example 4

Synthesis of 4-{2-[[6-(2,4-difluorophenyl)-2-pyridinyl]oxy]ethoxy}benzaldehyde

To a toluene (80 mL) solution containing 4-{2-[(6-bromo-2-pyridinyl)oxy]ethoxy}benzaldehyde (1 g) and tetrakis(triphenylphosphine)palladium (0.18 g), a 2M aqueous solution (4 mL) of sodium carbonate and a solution of 2,4-difluorophenylbenzeneboronic acid (0.64 g) in ethanol (4 mL) were added. The resultant mixture was refluxed for four hours. After completion of reaction, the reaction mixture was poured into saturated saline, and the thus-obtained toluene layer of the resultant mixture was separated. The separated layer was dried over magnesium sulfate, and the residual solvent was removed through distillation under reduced pressure. The thus-yielded residue was purified by means of a silica gel column, to thereby yield 0.71 g of the title compound as colorless crystals (yield 64.5%).

$^1$H-NMR (CDCl$_3$, δ): 4.45(2H, t, J=4.9 Hz), 4.81(2H, t, J=4.9 Hz), 6.77(1H, d, J=7.8 Hz), 6.88–6.94(1H, m), 6.97–7.01(1H, m), 7.07(2H, d, J=8.8 Hz), 7.42(1H, dd, J=7.8,2.0 Hz), 7.67(1H, t, J=7.8 Hz), 7.84(2H, d, J=8.8 Hz), 8.01–8.08(1H, m), 9.89(1H, s).

Example 1

Production of 5-2-[4-(1H-imidazolylmethyl)phenoxy]ethoxy-2,3-diphenylpyrazine (Compound 1A of the present invention)

(4-(2-[(5,6-Diphenyl-2-pyrazinyl)oxy]ethoxy)phenyl)methanol (15.42 g) was dissolved in dichloromethane (360 mL). A catalytic amount of dimethylformamide and thionyl chloride (9.0 mL) were added to the above solution, and the resultant mixture was stirred at room temperature for two hours. Then, the solvent and an excessive amount of thionyl chloride were removed through distillation under reduced pressure. Imidazole (13.17 g) and dimethylformamide (80 mL) were added to the residue, and the mixture was heated at 90° C. for two hours under stirring. Subsequently, water was added to the reaction mixture, and the thus-formed organic matter was separated through extraction by use of chloroform, followed by washing with water. The washed product was dried over sodium sulfate anhydrate, and the residual solvent was removed through distillation under reduced pressure. The thus-yielded residue was purified by means of a silica gel column and crystallized from n-propanol, to thereby yield 13.0 g of Compound (1A) of the present invention as colorless crystals (yield 80.0%).

Example 2

In a manner similar to that employed in Example 1, the following compounds of the present invention were produced: (1C), (1D), (1E), (1F), (1G), (1H), (1I), (1K), (1M), (1N), (1S), (1T), (1U), (1V), (1W), (1X), (1Z), (1AA), (1AB), (1AC), (1AD), (1AE), (1AF), (1AG), (1AH), (1AI), (1AK), (1AL), (1AM), (1AN), (1AP), (1AQ), (1AR), (1AS), (1AT), (1AU), (1AV), (1AW), (1AX), (1AY), (1AZ), (1BA), (1BB), (1BC), (1BD), (1BE), (1BF), (1BG), (1BH), (1BI), (1BJ), (1BK), (1BL), (1BM), (1BN), (1BO), (1BP), (1BQ), (1BR), (1BS), (1BT), (1BU), (1BV), (1BW), (1BX), (1BY), (1BZ), (1CA), (1CB), (1CC), (1CD), (1CE), (1CF), (1CG), (1CH), (1CI), and (1CJ).

Example 3

Production of 5-(2-[4-(1H-imidazolylmethyl)phenoxy]ethoxy)-2,3-di(2-pyridyl)pyrazine (Compound 1B of the present invention)

5,6-Di(2-pyridyl)-2-pyrazinol (1.21 g), 2-[4-(1H-imidazolylmethyl)phenoxy]-1-ethanol (1.05 g), and triphenylphosphine (1.27 g) were dispersed in tetrahydrofuran (30 mL). A 40% solution (2.10 g) of diethyl azodicarboxylate in toluene was added dropwise to the dispersion under ice cooling, and the resultant mixture was allowed to react overnight, while the temperature of the mixture was gradually elevated to room temperature. After completion of reaction, ethyl acetate was added to the reaction mixture, and the ethyl acetate layer was washed with water. The washed product was dried over sodium sulfate anhydrate, and the residual solvent was removed through distillation under reduced pressure. The thus-yielded residue was purified by means of a silica gel column and recrystallized from ethyl acetate, to thereby yield 960 mg of Compound (1B) of the present invention as pale yellow crystals (yield 44.0%).

Example 4

In a manner similar to that employed in Example 3, the following compounds of the present invention were produced: (1Q), (1Y), (1AE), (1AJ), and (1AO).

Example 5

Production of 5-(3-[4-(1H-imidazolylmethyl)phenoxy]propyl)-2,3-diphenylpyrazine (Compound 1R of the present invention)

3-(5,6-Diphenyl-2-pyrazinyl)-1-propanol (950 mg), 4-(1H-imidazolylmethyl)phenol (570 mg), and triphenylphosphine (860 mg) were suspended in anhydrous tetrahydrofuran (30 mL). A 40% solution (1.56 g) of diethyl azodicarboxylate in toluene was added dropwise to the resultant suspension under ice cooling, and the resultant mixture was stirred at room temperature for one hour. Ethyl acetate was added to the mixture, and the ethyl acetate layer was washed sequentially by a 10% aqueous solution of sodium hydroxide, water, and saturated saline. The washed product was dried over sodium sulfate anhydrate, and the residual solvent was removed through distillation under reduced pressure. The thus-yielded residue was purified by means of a silica gel column and crystallized from ether, to thereby yield 500 mg of Compound (1R) of the present invention as colorless crystals (yield 34.0%).

Example 6

In a manner similar to that employed in Example 5, Compounds (1O) and (1P) of the present invention were produced.

Example 7

Production of 5-(2-[4-(1H-imidazolylmethyl) phenoxy]ethyl)sulfinyl-2,3-diphenylpyrazine (Compound 1J of the present invention)

5-(2-[4-(1H-Imidazolylmethyl)phenoxy]ethyl)sulfanil-2,3-diphenylpyrazine (Compound 1I of the present invention) (464 mg) was dissolved in chloroform (20 mL), and m-chloroperbenzoic acid (260 mg) was added to the solution. The resultant mixture was stirred at room temperature for three hours. The reaction mixture was washed sequentially with an aqueous solution of saturated sodium bicarbonate and water. The washed product was dried over magnesium sulfate anhydrate, and the residual solvent was removed through distillation under reduced pressure. The thus-yielded residue was purified sequentially by means of an alumina column and a silica gel column, to thereby yield 410 mg of Compound (1J) of the present invention as colorless crystals (yield 85.4%).

Example 8

The procedure of Example 7 was repeated except that the amount of m-chloroperbenzoic acid was increased, to thereby yield Compound (1L) of the present invention.

TABLE 1
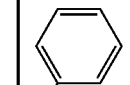
| R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|
| 1A 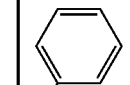 | 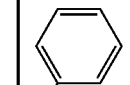 | N | N | CH | O | O | 4 | H | H | H | 2 | 1 | 132–135 | (CDCl₃): 4.37(2H, t, J=5.0 Hz), 4.81(2H, t, J=5.0 Hz), 5.05(2H, s), 6.87(1H, s), 6.95(2H, d, J=9.0 Hz), 7.08(2H, d, J=9.0 Hz), 7.12(1H, s), 7.25~7.46(10H, m), 7.52(1H, s), 8.32 (1H, s). |
| 1B 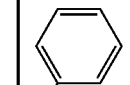 | 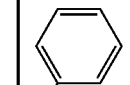 | N | N | CH | O | O | 4 | H | H | H | 2 | 1 | 118–120 | (CDCl₃): 4.37(2H, t, J=5.0 Hz), 4.83(2H, t, J=5.0 Hz), 5.05(2H, s), 6 88–6.89(3H, m), 7.06~7.10(3H, m), 7.12~7.24(2H, m), 7.53(1H, s), 7.61~7.76(4H, m), 8.37–8.39(3H, m). |
| 1C 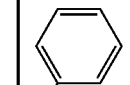 | 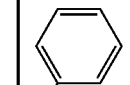 | N | N | CH | O | O | 4 | H | H | H | 2 | 1 | 90–95 (HClsalt) | (CDCl₃): 3.68(3H, s), 3.70(3H, s), 4.40(2H, t, J=4.9 Hz), 4.82(2H, t, J=4.9Hz), 5.37(2H, s), 6.83~7.19(9H, m), 7.21~7.36(5H, m), 8.31(1H, s), 9.24(1H, s). |
| 1D | | N | N | CH | O | O | 4 | H | H | H | 2 | 1 | 186–189 (HClsalt) | (CDCl₃): 4.39(2H, t, J=4.9 Hz), 4.81(2H, t, J=4.9 Hz), 5.42(2H, s), 6.98~7.06(7H, m), 7.33~7.44(7H, m), 8.30(1H, s), 9.49(1H, s).; HClsalt. |

TABLE 1-continued structure (1): R1-X1/R2-X2 ring with Y-(CH2)m-Z linker to A ring with R3, R4 substituents and (CH2)n-imidazole(R5)

| R1 | R2 | X1 | X2 | A | Y | Z | Locant of (CH2)n | R3 | R4 | R5 | m | n | m.p. (°C) | NMR (δ ppm) |
|---|---|---|---|---|---|---|---|---|---|---|---|---|---|---|
| 1E | 2-thienyl | N | CH | N | O | O | 4 | H | H | H | 2 | 1 | 150–151 | (CDCl₃): 4.34(2H, t, J=4.9 Hz), 4.75(2H, t, J=4.9 Hz), 5.05(2H, s), 6.67(1H, dd, J=1.0 Hz, 3.4 Hz), 6.84(1H, dd, J=3.4 Hz, 5.4 Hz), 6.88(1H, t, J=1.0 Hz), 6.94(2H, d, J=8.8 Hz), 7.07(1H, s), 7.09(2H, d, J=8.8 Hz), 7.29 (1H, dd, J=1.0 Hz, 5.4 Hz), 7.40~7.46(3H, m), 7.52~7.55(3H, m), 8.25(1H, s). |
| 1F | 4-Cl-phenyl | 4-Cl-phenyl | N | CH | N | O | O | 4 | H | H | H | 2 | 1 | 212–214 (HClsalt) | (CDCl₃): 4.39(2H, t, J=4.9 Hz), 4.81(2H, t, J=4.9 Hz), 5.36(2H, s), 7.00~7.02(2H, m), 7.07(1H, s), 7.26~7.40(11H, m), 8.32 (1H, s), 9.15(1H,s); HClsalt. |
| 1G | 4-CH₃-phenyl | 4-CH₃-phenyl | N | CH | N | O | O | 4 | H | H | H | 2 | 1 | 189–192.5 (HClsalt) | (CDCl₃): 2.34(3H, s), 2.36(3H, s), 4.38(2H, t, J=4.9 Hz), 4.81(2H, t, J=4.9 Hz), 5.37(2H, s), 7.0~7.12(7H, m), 7.26~7.37(7H, m), 8.27(1H, s), 9.27(1H, s); HClsalt. |

TABLE 2
| | $R^1$ | $R^2$ | $X^1$ | $X^2$ | A | Y | Z | Locant of $(CH_2)_n$ | $R^3$ | $R^4$ | $R^5$ | m | n | m.p. (° C.) | NMR (δ ppm) |
|---|---|---|---|---|---|---|---|---|---|---|---|---|---|---|---|
| 1H |  | 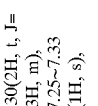 | N | N | CH | O | O | 4 | H | H | H | 2 | 1 | 170–172 (HClsalt) | (CDCl$_3$): 2.30(3H, s), 2.31(3H, s), 4.38(2H, t, J=4.9 Hz), 4.82(2H, t, J=4.9 Hz), 5.45 (2H, s), 6.98~7.17(9H, m), 7.31~7.36(5H, m), 8.29(1H, s), 9.71(1H, brs) 15.90(1H, br s).; HClsalt. |
| 1I | | 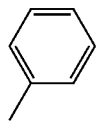 | N | N | CH | S | O | 4 | H | H | H | 2 | 1 | 97~99 | (CDCl$_3$): 3.65(2H, t, J=6.8 z), 4.30(2H, t, J=6.8 Hz), 5.00(2H, s), 6.86~6.90(3H, m), 6.94~6.97(2H, m), 7.07(1H, s), 7.25~7.33 (6H, m), 7.38~7.44(4H,m), 7.50(1H, s), 8.50 (1H, s). |
| 1J | | 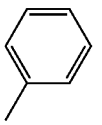 | N | N | CH | SO | O | 4 | H | H | H | 2 | 1 | 56–60 | (CDCl$_3$): 3.54~3.60(1H, m), 3.63~3.69 (1H, m), 4.43~4.48(1H, m), 4.55~4.60(1H, m), 5.00(2H, s), 6.69~6.72(2H, m), 6.82 (1H, s), 7.01~7.03 (2H, m), 7.06(1H, s), 7.29~7.49(11H, m), 9.14(1H, s). |
| 1K | | | N | N | CH | O | O | 4 | H | H | H | 2 | 1 | 128–130 | (CDCl$_3$): 4.37(2H, t, J=4.9 Hz), 4.80(2H, t, J=4.9 Hz), 5.05(2H, s), 6.89(1H, brs), 6.94 (2H, d, J=8.3 Hz), 7.08(1H, s), 7.11(2H, d, J=8.3 Hz), 7.28~7.38(5H, m), 7.50~7.60 (5H, m), 8.36(1H, s). |

TABLE 2-continued

| R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|
| 1L | phenyl | phenyl | N | N | CH | SO₂ | O | 4 | H | H | H | 2 | 1 | 135–137 | (CDCl₃): 3.95(2H, t, J=5.9 Hz), 4.50(2H, t, J=5.9 Hz), 4.98(2H, s), 6.54–6.56(2H, m), 6.80(1H, s), 6.95–6.97(2H, m), 7.05(1H, s), 7.26–7.48(11H, m), 9.18(1H, s) |
| 1M | phenyl | 4-CF₃-phenyl | N | N | CH | O | O | 4 | H | H | H | 2 | 1 | amorphous | (CDCl₃): 4.38(2H, t, J=4.9 Hz), 4.82(2H, t, J=4.9 Hz), 5.06(2H, s), 6.88(1H, s), 6.95 (2H, d, J=8.8 Hz), 7.08(1H, s), 7.11(2H, d, J=8.8 Hz), 7.26–7.55(10H, m), 8.33(1H, s). |
| 1N | phenyl | phenyl | N | N | CH | O | O | 4 | H | H | H | 3 | 1 | 91–92 | (CDCl₃): 2.29–2.35(2H, dt, J=6.4 Hz), 4.17 (2H, t, J=6.4 Hz), 4.64(2H, t, J=6.4 Hz), 5.03 (2H, s), 6.87–6.90 (3H, m), 7.06–7.10(3H, m), 7.25–7.31(6H, m), 7.33–7.38(2H, m), 7.43–7.45(2H, m), 7.52(1H, s), 8.24 (1H, s). |
| 1O | phenyl | phenyl | N | N | CH | NH | O | 4 | H | H | H | 2 | 1 | 147–148.5 | (CDCl₃): 3.90–3.94(2H, m), 4.20(2H, t, J=5.4 Hz), 5.05(2H, s), 5.10(1H, br), 6.88(1H, s), 6.91–6.93(2H, m), 7.08–7.11(3H, m), 7.23–7.35 (8H, m), 7.42–7.44(2H, m), 7.52 (1H, s), 8.00(1H, s). |

TABLE 3
| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1P |  | 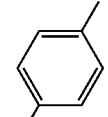 | N | N | CH | N—CH₃ | O | 4 | H | H | H | 2 | 1 | 93–96 | (CDCl₃): 3.30(3H, s), 4.06(2H, t, J=5.9 Hz), 4.24 (2H, t, J=5.9Hz), 5.02(2H, s), 6.86–6.90(3H, m), 7.03–7.07 (3H, m), 7.22–7.36(8H, m), 7.41–7.44 (2H, m), 7.51(1H, s), 8.09(1H, s). |
| 1Q |  |  | N | CH | | O | O | 4 | H | H | H | 2 | 1 | 67–71 | (CDCl₃): 4.38(2H, t, J=4.9 Hz), 4.82(2H, t, J=4.9 Hz), 5.05 (2H, s), 6.88(1H, s), 6.94(2H, d, J=8.8 Hz), 7.04(1H, s), 7.12(2H, d, J=8.8 Hz), 7.48–7.60(9H, m), 8.38(1H, s). |
| 1R | | | N | CH | | CH₂ | O | 4 | H | H | H | 2 | 1 | 91–92 | (CDCl₃): 2.32–2.38(2H, m), 3.11 (2H, t, J=7.3 Hz), 4.09(2H, t, J= 6.4 Hz), 5.04(2H, s), 6.87–6.89 (3H, m), 7.07–7.09(3H, m), 7.26–7.32(6H, m), 7.40–7.44 (4H, m), 7.52(1H, s), 8.49(1H, s). |
| 1S | | | N | CH | | O | CH₂ | 4 | H | H | H | 1 | 1 | 202–205 | (CDCl₃): 3.14(2H, t, J=7.3 Hz), 4.63(2H, t, J=7.3 Hz), 5.28(2H, s), 6.90(1H, s), 7.08–7.12 (3H, m), 7.25–7.45(12H, m), 7.54(1H, s), 8.22(1H, s). |

TABLE 3-continued

| R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|
| 1T | phenyl | phenyl | N | N | CH | O | O | 3 | H | H | H | 2 | 1 | 93–94 | (CDCl₃): 4.33(2H, t, J=4.8 Hz), 4.79(2H, t, J=4.8 Hz), 5.07(2H, s), 6.73–6.90 (4H, m), 7.08 (1H, s), 7.27–7.54 (12H, m), 8.31(1H, s). |
| 1U | phenyl | phenyl | N | N | CH | O | O | 4 | NH₂ | H | H | 2 | 1 | 123–126 | (CDCl₃): 4.38(2H, t, J=4.9 Hz), 4.83 (2H, t, J=4.9 Hz), 4.88(2H, brs), 5.05(2H, s), 6.88(1H, s), 6.93–6.96(2H, m), 7.08(1H, s), 7.10–7.12(2H, m), 7.21–7.26 (7H, m), 7.33–7.36(3H, m), 7.53(1H, s). |
| 1V | phenyl | phenyl | N | N | CH | O | O | 4 | H | H | 2-CH₃ | 2 | 1 | 144–146 | (CDCl₃): 2.34(3H, s), 4.36(2H, t, J=4.8 Hz), 4.80(2H, t, J=4.8 Hz), 4.97(2H, s), 6.81(1H, s), 6.92–7.01(5H, m), 7.26–7.46(10H, m), 8.31(1H, s). |
| 1W | phenyl | phenyl | N | CH | CH | O | O | 4 | H | H | H | 2 | 1 | Oil | (CDCl₃): 4.35(2H, t, J=4.9 Hz), 4.78(2H, t, J=4.9 Hz), 5.03(2H, s), 6.83(1H, d, J=8.3 Hz), 6.87(1H, s), 6.95(2H, d, J=8.8 Hz), 7.07 (1H, s), 7.08(2H, d, J=8.8 Hz), 7.14(2H, d, J=7.8 Hz), 7.18–7.30 (6H, m), 7.37(2H, d, J=5.9 Hz), 7.52(1H, s), 7.63 (1H, d, J=8.3 Hz). |

TABLE 4
| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1X | 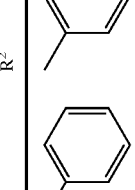 | 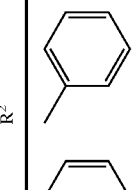 | N | N | CH | O | O | 4 | H | 2-OCH₃ | H | 2 | 1 | 108–109 | (CDCl₃): 3.80(3H, s), 4.44(2H, t, J=4.9 Hz), 4.83(2H, t, J=4.9 Hz), 5.05(2H, s), 6.65~6.70 (2H, m), 6.89(1H, s), 6.96(1H, d, J=8.3 Hz), 7.09(1H, s), 7.26~7.39(8H, m), 7.43~7.45 (2H, m), 7.54(1H, s), 8.30(1H, s). |
| 1Y | 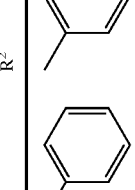 | 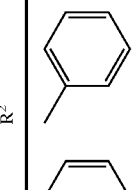 | N | N | CH | O | O | 4 | H | H | H | 2 | 0 | 135–138 | (CDCl₃): 4.42(2H, t, J=4.4 Hz), 4.85 (2H, t, J=4.4 Hz), 7.05~7.07(2H, m), 7.19(1H, s), 7.21(1H, s), 7.28~7.47 (12H, m), 7.77(1H, s), 8.33(1H, s). |
| 1Z | 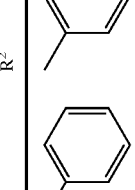 | 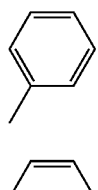 | N | CH | CH | O | O | 4 | H | H | H | 2 | 1 | 126–127.5 | (CDCl₃): 4.36(2H, t, J=4.9 Hz), 4.80 (2H, t, J=4.9Hz), 5.04(2H, s), 6.73~6.82 (2H, m), 6.84(1H, d, J=8.3 Hz), 6.88 (1H, t, J=1.5 Hz), 6.94~6.97(2H, m), 7.04~7.10(4H, m), 7.22~7.29(3H, m), 7.34~7.36(2H, m), 7.52(1H, s), 7.58(1H, dd, J=8.3, 1.0 Hz). |
| 1AA | 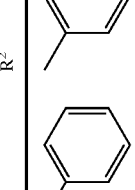 | 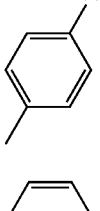 | N | CH | CH | O | O | 4 | H | H | H | 2 | 1 | 125–127.5 (Fumarate) | (CDCl₃): 4.34(2H, t, J=4.8 Hz), 4.67 (2H, t, J=4.8 Hz), 5.12(2H, s), 6.91~6.99 (4H, m), 7.12~7.3l(12H, m), 7.74 (1H, d, J=8.3 Hz), 7.80(1H, s).Fumarate |

TABLE 4-continued

| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1AB | phenyl | phenyl | N | N | CH | O | CH₂ | 4 | H | H | H | 2 | 1 | 147–148 | (CDCl₃): 2.12–2.19 (2H, m), 2.83(2H, t, J=7.8 Hz), 4.45(2H, t, J=6.4 Hz), 5.08 (2H, s), 6.89(1H, s), 7.07–7.09(3H, m), 7.21–7.44(12H, m), 7.54(1H, s), 8.24(1H, s). |
| 1AC | phenyl | phenyl | N | N | CH | O | O | 4 | Cl | H | H | 2 | 1 | 144.5–146 | (CDCl₃): 4.41(1H, t, J=4.9 Hz), 4.86 (2H, t, J=4.9 Hz) 5.05(2H, s), 6.88(1H, s), 6.95–6.97(2H, m), 7.07(1H, s), 7.09–7.11 (2H, m), 7.26–7.43(10H, m), 7.52(1H, s). |
| 1AD | phenyl | H | N | N | CH | O | O | 4 | H | H | H | 2 | 1 | 89–91 | (CDCl₃): 4.39 (2H, t, J=4.9 Hz), 4.83(2H, t, J=4.9 Hz) 5.05(2H, s), 6.88(1H, s), 6.93–6.96 (2H, m), 7.07(1H, s), 7.10–7.13(2H, m), 7.46–7.52(4H, m), 8.00–8.03(2H, m), 8.22 (1H, s), 8.63(1H, s). |

TABLE 5

| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1AE | 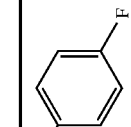 | 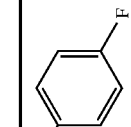 | N | N | CH | O | O | 4 | H | H | H | 2 | 0 | 149.5–151 | (CDCl₃): 4.42(2H, t, J=4.9 Hz), 4.83 (2H, t, J=4.9 Hz), 6.98~7.06(6H, m), 7.19(1H, s), 7.21(1H, s), 7.31~7.37(4H, m), 7.41~7.45 (2H, m), 7.77(1H, s), 8.31 (1H, s). |
| 1AF | 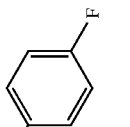 | 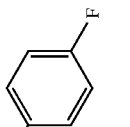 | N | CH | CH | O | O | 4 | H | H | H | 2 | 1 | 133~138 (3/2Fumarate) | (DMSO-d₆): 4.35(2H, t, J=4.4 Hz), 4.69(2H, t, J=4.4 Hz), 5.11(2H, s), 6.62(2H, s), 6.91(1H, s), 6.97~7.00(3H, m), 7.13~7.23(7H, m), 7.30~7.33(1H, m), 7.68(1H, dt, J=7.8, 2.0 Hz), 7.78(1H, s), 7.79(1H, d, J=8.8 Hz), 8.46~8.47(2H, m). Fumarate |
| 1AG | 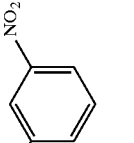 | 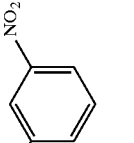 | N | CH | CH | O | O | 4 | H | H | H | 2 | 1 | 93–95 (Fumarate) | (DMSO-d₆): 4.36(2H, t, J=4.9 Hz), 4.70(2H, t, J=4.9 Hz), 5.11(2H, s), 6.62(2H, s), 6.90(1H, s), 6.97~6.99(3H, m), 7.15(1H, s), 7.21(2H, d, J=8.8 Hz), 7.27~7.33(5H, m), 7.53~7.57(2H, m), 7.74(1H, s), 7.87(1H, d, J=8.3 Hz), 7.96(1H, brs), 8.09~8.12(1H, m).Fumarate |
| 1AH | 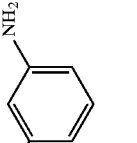 | 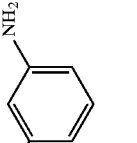 | N | CH | CH | O | O | 4 | H | H | H | 2 | 1 | 105–113 (2 Fumarate) | (DMSO-d₆): 4.35(2H, t, J=4.9 Hz), 4.67 (2H, t, J=4.9 Hz), 5.13(2H, s), 6.22 (1H, d, J=7.8 Hz), 6.42(1H, t, J=2.0 Hz), 6.46(1H, dd, J=7.8, 2.0 Hz), 6.63(4H, s), 6.86(1H, dd, J=8.3 Hz), 6.90(1H, t, J=7.8 Hz), 6.95 (1H, s), 6.99(2H, d, J=8.8 Hz), 7.19~7.25(6H, m), 7.38~7.40(2H, m), 7.46(1H, d, J=8.3 Hz), 8.30(1H, brs). Fumarate |
| 1AI | 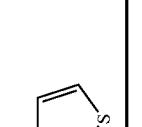 | 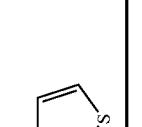 | N | CH | CH | O | O | 4 | H | H | H | 2 | 1 | oil | (CDCl₃): 4.34(2H, t, J=4.8 Hz),4.77(2H, t, J=4.8 Hz), 5.03(2H, s),6.67–6.72(1H, m), 6.79(1H, d, J=8.3Hz), 6.87(1H, s), 6.90~6.95 (2H, m), 7.02~7.18(4H, m), 7.24~7.45 (5H, m), 7.51(1H, s), 7.66~7.79(2H, m). |

TABLE 6

| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1AJ | (3-methylphenyl) | (phenyl) | N | N | CH | O | O | 4 | H | H | H | 3 | 0 | 162~164 (1/2 Fumarate) | (DMSO-d₆): 2.27(2H, q, J=6.4 Hz), 4.21(2H, t, J=6.4 Hz), 4.60(2H, t, J=6.3 Hz), 6.62 (1H, s), 7.04~7.08(3H, m), 7.29~7.59 (13H, m), 8.09(1H, s), 8.35(1H, s), 12.97(br).Fumarate |
| 1AK | (3-methylphenyl) | H | N | CH | CH | O | O | 4 | H | H | H | 2 | 1 | 118~120 | (CDCl₃): 4.37(2H, t, J=4.9 Hz), 4.82 (2H, t, J=4.9 Hz), 5.03 (2H, s), 6.74 (1H, d, J=7.8 Hz), 6.95(2H, d, J=8.8 Hz), 7.07(1H, s), 7.10 (2H, d, J=8.8 Hz), 7.35~7.47(4H, m), 7.51(1H, t, J=7.8 Hz), 8.00~8.03 (2H, m). |
| 1AL | H | (2,4-difluorophenyl) | N | CH | CH | O | O | 4 | H | H | H | 2 | 1 | 94~94.5 | (CDCl₃): 4.34(2H, t, J=5.4 Hz), 4.72(2H, t, J=5.4 Hz), 5.05(2H, s), 6.86~6.99(6H, m), 7.07(1H, s), 7.11(2H, d, J=8.8 Hz), 7.33~7.39(1H,m), 7.52(1H, s), 7.72~7.74(1H, m), 8.26 (1H, brs). |
| 1AM | H | (3-methylphenyl) | N | CH | CH | O | O | 4 | H | H | H | 2 | 1 | 140~141 | (CDCl₃): 4.34(2H, t, J=5.3 Hz), 4.72(2H, t, J=4.8 Hz), 5.04(2H, s), 6.86~6.96(4H, m), 7.06~7.12(3H, m), 7.35~7.53(5H, m), 7.79~7.82(1H, m), 8.01(1H, s), 8.36~8.37(1H, m). |
| 1AN | H | (3-methylphenyl) | N | CH | CH | O | O | 4 | H | H | H | 2 | 1 | 163~164.5 | (CDCl₃): 4.36 (2H, t, J=4.9 Hz), 4.74(2H, t, J=4.9 Hz), 5.05(2H, s), 6.88(1H, s), 6.93~6.96 (2H, m), 7.07(1H, s), 7.11~7.13(2H, m), 7.39~7.50(3H, m), 7.52(1H, m), 7.91~7.93(2H, m), 8.36(1H, d, J=1.5 Hz), 8.51(1H, d, J=1.5 Hz). |
| 1AO | (3-methylphenyl) | H | N | N | CH | O | O | 4 | H | H | H | 3 | 0 | 88~89 | (CDCl₃): 2.34~2.40(2H, m), 4.22(2H, t, J=5.9 Hz), 4.68(2H, t, J=5.9 Hz), 6.99~7.01(2H, m), 7.18(1H, s), 7.19(1H, s), 7.26~7.30(2H, m), 7.45~7.51(3H, m), 7.75(1H, s), 8.01~8.03(2H, m), 8.16(1H, s), 8.60(1H, s). |

TABLE 7

| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1AP | 4-F-phenyl | H | N | N | CH | O | O | 4 | H | H | H | 2 | 1 | 80~81 | (CDCl₃): 4.38(2H, t, J=4.9 Hz), 4.81(2H, t, J=4.9 Hz), 5.05 (2H, s), 6.88(1H, s), 6.93~6.95(2H, m), 7.08(1H, s), 7.11~7.13(2H, m), 7.16~7.20 (2H, m), 7.52(1H, s), 7.99~8.02(2H, m), 8.21(1H, s),8.58(1H, s). |
| 1AQ | phenyl | 4-F-phenyl | N | N | CH | O | O | 4 | H | H | H | 2 | 1 | 130~131.5 | (CDCl₃): 4.36(2H, t, J=4.9 Hz), 4.73 (2H, t, J=4.9 Hz), 5.06(2H, s), 6.88(1H, s), 6.93~6.95 (2H, m), 7.07(1H, s), 7.11~7.18(4H, m), 7.52(1H, s), 7.88~7.91(2H, m), 8.32(1H, d, J=1.5 Hz), 8.46(1H, d, J=1.5 Hz). |
| 1AR | phenyl | phenyl | N | N | CH | O | O | 4 | H | H | 4-NO₂ | 2 | 1 | 61-65 | (DMSO-d₆): 4.40(2H, t, J=4.4 Hz), 4.74 (2H, t, J=4.4 Hz), 5.22(2H, s), 7.00~7.02 (2H, m), 7.28~7.40(12H, m), 7.94(1H, d, d=1.4 Hz), 8.38(1H, s), 8.40(1H, d, J=1.4 Hz). |
| 1AS | thienyl | thienyl | N | CH | CH | O | O | 4 | H | H | H | 2 | 1 | 94~97 | (CDCl₃): 4.35(2H, t, J=4.4 Hz), 4.78(2H, t, J=4.8 Hz), 5.04(2H, s), 6.74(1H, d, J=8.3 Hz), 6.86~6.87(2H, m), 6.94~6.96(2H, m), 7.07~7.16(6H, m), 7.27~7.30(2H, m), 7.52(1H, s), 7.58(1H, d, J=8.3 Hz). |
| 1AT | 2,4-diF-phenyl | H | N | N | CH | O | O | 4 | H | H | H | 2 | 1 | 154.5-157.5 | (CDCl₃): 4.36(2H, t, J=4.9 Hz), 4.75(2H, t, J=4.9 Hz), 5.06(2H, s), 6.88(1H, s), 6.91~7.03(4H, m), 7.07 (1H, s), 7.11~7.13(2H, m), 7.52(1H, s), 7.93~7.99 (1H, m), 8.36(1H, d, J=1.5 Hz), 8.55~8.56 (1H, m). |
| 1AU | phenyl | phenyl | N | N | CH | O | O | 4 | H | H | 4-NH₂ | 2 | 1 | 90~93 | (CDCl₃): 4.37(2H, t, J=4.9 Hz), 7.81 (2H, t, J=4.9 Hz), 4.90 (2H, s), 6.16(1H, d, J=1.5 Hz), 6.92~6.94(2H, m), 7.09~7.11(2H, m), 7.16(1H, d, J=1.0 Hz), 7.26~7.46 (10H, m), 8.31(1H, s). |

TABLE 8

| | $R^1$ | $R^2$ | $X^1$ | $X^2$ | A | Y | Z | Locant of $(CH_2)_n$ | $R^3$ | $R^4$ | $R^5$ | m | n | m.p. (° C.) | NMR (δ ppm) |
|---|---|---|---|---|---|---|---|---|---|---|---|---|---|---|---|
| 1AV |  | 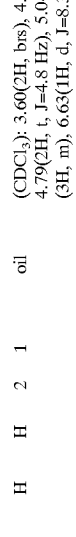 | N | CH | CH | O | O | 4 | H | H | H | 2 | 1 | oil | (CDCl$_3$): 4.37(2H, t, J=4.8 Hz), 4.80(2H, t, J=4.8 Hz), 5.05(2H, s), 6.82(1H, d, J=8.3Hz), 6.88(1H, s), 6.94–6.97(3H, m), 7.07–7.21 (5H, m), 7.49–7.58 (4H, m), 8.13(1H, s), 8.15–8.20(1H, m). |
| 1AW | 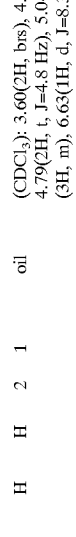 |  | N | CH | CH | O | O | 4 | H | H | H | 2 | 1 | oil | (CDCl$_3$): 3.60(2H, brs), 4.36(2H, t, J=4.8 Hz), 4.79(2H, t, J=4.8 Hz), 5.04(2H, s), 6.45–6.56 (3H, m), 6.63(1H, d, J=8.3 Hz), 6.77(1H, s), 6.84–6.86(2H, m), 6.97–7.06(5H, m), 7.15–7.19(2H, m), 7.41(1H, d, J=8.3 Hz), 7.46(1H, s). |
| 1AX | H |  | N | CH | CH | O | O | 4 | H | H | H | 2 | 1 | 156–157.5 | (CDCl$_3$): 3.85(3H, s), 4.34(2H, t, J=4.8 Hz), 4.70(2H, t, J=4.8 Hz), 5.04(2H, s), 6.83–7.12 (9H, m), 7.43–7.52(3H, m), 7.75–7.76(1H, m), 8.31(1H, d, J=2.4 Hz). |
| 1AY | H |  | N | CH | CH | O | O | 4 | H | H | H | 2 | 1 | 125–128 | (CDCl$_3$): 4.37(2H, t, J=4.9 Hz), 4.76(2H, t, J=4.9 Hz), 5.06(2H, s), 6.88(1H, s), 6.93–6.95(2H, m), 7.08(1H, s), 7.12–7.14(2H, m), 7.53(1H, s), 7.73(2H, d, J=8.3 Hz), 8.05(2H, d, J=8.3 Hz), 8.37(1H, d, J=1.5 Hz), 8.55(1H, d, J=1.5 Hz). |
| 1AZ | H |  | N | CH | CH | O | O | 4 | H | H | H | 2 | 1 | 160–161 | (CDCl$_3$): 2.41 (3H, s), 4.35(2H, t, J=4.9 Hz), 4.73(2H, t, J=4.9 Hz), 5.06(2H, s), 6.88 (1H, t, J=1.5 Hz), 6.93–6.96(2H, m), 7.07(1H, s), 7.11–7.13(2H, m), 7.29(2H, d, J=8.3 Hz), 7.53(1H, s), 7.81(2H, d, J=8.3 Hz), 8.33(1H, d, J=1.5 Hz), 8.48(1H, d, J=1.5 Hz). |
| 1BA |  | H | N | CH | CH | O | O | 4 | H | H | H | 2 | 1 | 127–129 | (CDCl$_3$): 4.37(2H, t, J=4.9 Hz), 4.78(2H, t, J=4.9 Hz), 5.06(2H, s), 6.88(1H, s), 6.93–7.04(4H, m), 7.08(1H, s), 7.11–7.13(2H, m), 7.52(1H, s), 8.00–8.06(1H, m), 8.24(1H, s), 8.67(1H, d, J=2.0 Hz). |

TABLE 9

| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1BB | 4-CH₃-C₆H₄ | H | N | N | CH | O | O | 4 | H | H | H | 2 | 1 | 119–120 | (CDCl₃): 2.43(3H, s), 4.38(2H, t,J=4.9 Hz), 4.82 (2H, t, J=4.9 Hz), 5.05(2H, s), 6.88(1H, s), 6.93–6.96(2H, m), 7.07(1H, s), 7.11–7.13(2H, m), 7.30(2H, d, J=8.3 Hz), 7.53 (1H, s), 7.91 (2H, d, J=8.3 Hz), 8.18(1H, s), 8.60(1H, s). |
| 1BC | 4-OMe-C₆H₄ | H | N | N | CH | O | O | 4 | H | H | H | 2 | 1 | 125–127 | (CDCl₃): 3.88(3H, s), 4.38 (2H, t, J=4.9 Hz), 4.81 (2H, t, J=4.9 Hz), 5.05(2H, s), 6.93(1H, s), 6.94(2H, d, J=8.8 Hz), 7.01(2H, d, J=8.8 Hz), 7.07(1H, s), 7.12(2H, d, J=8.8 Hz), 7.52(1H, s), 7.98(2H, d, J=8.8 Hz), 8.15 (1H, s), 8.57(1H, s). |
| 1BD | 4-CF₃-C₆H₄ | H | N | N | CH | O | O | 4 | H | H | H | 2 | 1 | 85–87 | (CDCl₃): 4.39(2H, t, J=4.9 Hz), 4.83(2H, t, J=4.9 Hz), 5.06(2H, s), 6.88 (1H, s), 6.94(2H, d, J=8.8 Hz), 7.08(1H, s), 7.12(2H, d, J=8.8 Hz), 7.52(1H, s), 7.75(2H, d, J=8.3 Hz), 8.13 (2H, d,J=8.3 Hz), 8.29(1H, s), 8.67(1H, s). |
| 1BE | C₆H₅ | H | N | N | CH | CH₂ | CH₂ | 4 | H | H | H | 2 | 1 | 96.5–99 (3/2 Fumarate) | (DMSO-d₆): 1.64–1.80(4H, m), 2.63(2H, t, J=7.3 Hz), 2.88(2H, t, J=7.8 Hz), 5.13(2H, s), 6.62(1.5H, s), 6.89(1H, s), 7.13–7.19(5H, m), 7.27–7.36(10H, m), 7.72(1H, s), 8.56(1H, s). Fumarate |
| 1BF | 3,4-F₂-C₆H₃ | H | N | N | CH | O | O | 4 | H | H | H | 2 | 1 | 85–87 | (CDCl₃): 4.38(2H, t, J=4.9 Hz), 4.81(2H, t, J=4.9 Hz), 5.05(2H, s), 6.88–6.95 (3H, m), 7.07–7.13(3H, m), 7.24–7.31(1H, m), 7.52(1H, s), 7.72–7.76(1H, m), 7.83–7.89(1H, m), 8.23 (1H, m), 8.57(1H, s). |
| 1BG | 3,5-F₂-C₆H₃ | H | N | N | CH | O | O | 4 | H | H | H | 2 | 1 | 112–115 | (CDCl₃): 4.38(2H, t, J=4.8 Hz), 4.81(2H, t, J=4.8 Hz), 5.05(2H, s), 6.88–6.95 (4H, m), 7.07–7.13(3H, m), 7.51–7.55(3H, s), 8.27(1H, s), 8.59(1H, s). |

TABLE 10

| | R¹ | R² | X¹ | X² | A | Y | Z | Locant of (CH₂)ₙ | R³ | R⁴ | R⁵ | m | n | m.p. (° C.) | NMR (δ ppm) |
|---|---|---|---|---|---|---|---|---|---|---|---|---|---|---|---|
| 1BH | 3-thienyl | H | N | N | CH | O | O | 4 | H | H | H | 2 | 1 | 108~111 | (CDCl₃): 4.37(2H, t, J=4.8 Hz), 4.78(2H, t, J=4.8 Hz), 5.05(2H, s), 6.88~6.95 (3H, m), 7.07~7.12(3H, m), 7.42~7.44(1H, m), 7.52(1H, s), 7.63~7.65(1H, m), 7.95~7.96(1H, m), 8.15(1H, s), 8.50(1H, s). |
| 1BI | 2,4-difluorophenyl | H | N | CH | CH | O | CH₂ | 4 | H | H | H | 2 | 1 | 61-63 | (CDCl₃): 2.08~2.15(2H, m), 2.81(2H, t, J=7.3 Hz), 4.34(2H, t, J=6.4 Hz), 5.08(2H, s), 6.80(1H, d, J=8.8 Hz), 6.90~6.98 (3H, m), 7.08~7.09(3H, m), 7.22(2H, d, J=8.3 Hz), 7.33~7.39(1H, m), 7.54(1H, s), 7.71~7.74(1H, m), 8.26(1H, s). |
| 1BJ | 2,4-difluorophenyl | H | CH | N | CH | O | O | 4 | H | H | H | 2 | 1 | 125-128.5 | (CDCl₃): 4.35~4.37(2H, m), 4.41-4.43 (2H, m), 5.06(2H, s), 6.87~7.01(5H, m), 7.08(1H, s), 7.13(2H, d, J=8.8 Hz), 7.32(1H, dd, J=8.8, 2.9 Hz), 7.53 (1H, s), 7.71(1H, dd, J=8.8, 2.0 Hz), 7.92~7.98(1H, m), 8.45(1H, d, J=2.9 Hz). |
| 1BK | phenyl | H | CH | CH | CH | O | O | 4 | H | H | H | 2 | 1 | 172-174.5 | (CDCl₃): 4.35-4.38(4H, m), 5.06(2H, s), 6.88(1H, s), 6.95(2H, d, J=8.3 Hz), 7.02 (2H, d, J=8.8 Hz), 7.08(1H, s), 7.12 (2H, d, J=8.3 Hz),7.31(1H, t, J=7.3 Hz), 7.42 (2H, t, J=7.3 Hz),7.52~7.57(5H, m). |
| 1BL | 4-methoxy-2-fluorophenyl | H | N | CH | CH | O | O | 4 | H | H | H | 2 | 1 | amorphous | (CDCl₃): 3.78(3H, s), 4.35(2H, t, J=4.8 Hz), 4.79 (2H, t, J=4.8 Hz), 5.04 (2H, s), 6.75~6.87(6H, m), 6.93~6.96 (2H, m), 7.05~7.11(4H, m), 7.29~7.31(2H, s), 7.54(1H, d, J=8.3 Hz). |
| 1BM | 1-naphthyl | H | N | CH | CH | O | O | 4 | H | H | H | 2 | 1 | 136-137.5 (Fumarate) | (DMSO-d₆): 4.36(2H, t, J=4.8 Hz), 4.67(2H, t, J=4.8 Hz), 5.13(2H, s), 6.92 (1H, s), 7.01(3H, t, J=8.3 Hz), 7.19(1H, s), 7.25(2H, d, J=8.7 Hz), 7.46(1H, d, J=6.8 Hz), 7.52~7.59(3H, m), 7.75~7.80(2H, m), 7.85(1H, dd, J=8.7, 2.4 Hz), 7.97~8.03(2H, m), 8.27(1H, d, J=2.4 Hz), Fumarate |

TABLE 11

| | R¹ | R² | X¹ | X² | A | Y | Z | Locant of (CH₂)ₙ | R³ | R⁴ | R⁵ | m | n | m.p. (°C.) | NMR(δ ppm) |
|---|---|---|---|---|---|---|---|---|---|---|---|---|---|---|---|
| 1BN | 2,4-difluorophenyl | H | N | CH | CH | O | O | 4 | H | H | H | 2 | 1 | 64–66 | (CDCl₃): 4.35(2H, t, J=4.9Hz), 4.76(2H, t, J=4.9Hz), 5.05(2H, s), 6.77(1H, d, J=7.8Hz), 6.88–7.00(5H, m), 7.07(1H, s), 7.10(2H, d, J=8.8Hz), 7.41(1H, dd, J=7.8, 1.5Hz), 7.52(1H, s), 7.65(1H, t, J=7.8Hz), 8.02–8.08(1H, m). |
| 1BO | phenyl | 4-SMe-phenyl | N | CH | CH | O | O | 4 | H | H | H | 2 | 1 | amorphous | (CDCl₃): 2.46(3H, s), 4.35(2H, t, J=4.8Hz), 4.78 (2H, t, J=4.8Hz), 5.03(2H, s), 6.81(1H, d, J=8.3Hz), 6.87(1H, s), 6.94–6.96 (2H, m), 7.04–7.14(7H, m), 7.23–7.26(3H, m), 7.37–7.39(2H, m), 7.52(1H, s), 7.60(1H, d, J=8.3Hz). |
| 1BP | H | 3,4-difluorophenyl | CH | CH | CH | O | O | 4 | H | H | H | 2 | 1 | 111–114 | (CDCl₃): 4.32–4.36(4H,m), 5.06(2H, s), 6.88–6.95(5H, m), 7.02(2H, d, J=8.8Hz), 7.08(1H,s), 7.12(2H, d, J=8.8Hz), 7.33–7.39 (1H, m), 7.44(2H, d, J=8.8Hz). |
| 1BQ | 3,4-difluorophenyl | H | CH | N | CH | O | O | 4 | H | H | H | 2 | 1 | HCl salt 158–162 | (DMSO-d₆): 4.37–4.39(2H, m), 4.52–4.54 (2H, m), 5.39(2H, s), 7.03(2H, d, J=8.3Hz), 7.25(1H, dt, J=8.3, 2.4Hz), 7.39–7.45(3H, m), 7.66(1H, t, J=1.5Hz), 7.70–7.77(3H, m), 8.43(1H, t, J=1.5Hz), 8.45(1H, d, J=2.4Hz), 9.34(1H, s). HCl salt |
| 1BR | H | 3,4-difluorophenyl | N | CH | CH | O | O | 4 | H | H | H | 2 | 1 | 94–96 | (CDCl₃): 4.34(2H, t, J=4.8Hz), 4.72(2H, t, J=4.8Hz), 5.05(2H, s), 6.85–6.88(2H, m), 6.93–6.96(2H, m), 7.07–7.12(3H, m), 7.21–7.33(3H, m), 7.52(1H, s), 7.73(1H, dd, J=8.5, 2.4Hz), 8.30(1H, d, J=2.4Hz). |
| 1BS | H | phenyl | CH | CH | CH | O | O | 4 | H | H | H | 2 | 1 | 102–103 | (CDCl₃): 4.34–4.41(4H,m), 5.05(2H, s), 6.88–7.37(19H, m), 7.52(1H, s). |

TABLE 12

| | R¹ | R² | X¹ | X² | A | Y | Z | Locant of (CH₂)ₙ | R³ | R⁴ | R⁵ | m | n | m.p. (°C) | NMR (δ ppm) |
|---|---|---|---|---|---|---|---|---|---|---|---|---|---|---|---|
| 1BT | H | 3,5-difluorophenyl | N | CH | CH | O | O | 4 | H | H | H | 2 | 1 | 113~115 | (CDCl₃): 4.34(2H, t, J=4.8Hz),4.72(2H, t, J=4.8Hz), 5.05(2H, s),6.77~6.81(1H, m), 6.87~6.89(2H, m),6.93~6.95(2H, m), 7.02~7.12(5H,m), 7.52(1H, s), 7.75(1H, dd, J=8.7,2.4Hz), 8.34(1H, d, J=2.4Hz). |
| 1BU | H | 4-CF₃-phenyl | N | CH | CH | O | O | 4 | H | H | H | 2 | 1 | 121~124 | (CDCl₃): 4.35(2H, t, J=4.8Hz),4.73(2H, t, J=4.8Hz), 5.05(2H, s),6.88~6.95(4H, m), 7.07(1H, s), 7.10~7.12(2H, m), 7.52(1H, s), 7.67(4H, dd,J=29, 8.7Hz), 7.82(1H, dd, J=8.7,2.4Hz), 8.39(1H, d, J=2.4Hz). |
| 1BV | H | 3-methylpyridinyl | CH | CH | CH | O | O | 4 | H | H | H | 2 | 1 | 141~143 | (CDCl₃): 4.33~4.39(4H, m), 5.06(2H,s), 6.89 (1H, s), 6.95(2H, d, J=8.3Hz),7.06(2H, d, J=8.8Hz), 7.08(1H, s),7.13(2H, d, J=8.8Hz), 7.35(1H, dd,J=7.8, 4.9Hz), 7.53(2H, d, J=8.3Hz), 7.54(1H, s), 7.84(1H, dt, J=7.8, 2.0Hz), 8.56(1H, dd, J=4.9, 2.0Hz),8.82(1H, d, J=2.0Hz). |
| 1BW | H | 1-ethylimidazolyl | CH | CH | CH | O | O | 4 | H | H | H | 2 | 1 | 139~140 | (CDCl₃): 4.31(4H, s), 5.05(4H, s),6.88(2H, s), 6.92(4H, d, J=8.8Hz),7.07(2H, s), 7.11(4H, d, J=8.8Hz),7.52(2H, s). |
| 1BX | CH₃ | H | N | CH | CH | O | O | 4 | H | H | H | 2 | 1 | 122~124 | (CDCl₃): 2.43(3H, s), 4.31(2H, t, J=4.8Hz), 4.66(2H, t, J=4.8Hz),5.04(2H, s), 6.57(1H, d, J=7.8Hz),6.72(1H, d, J=7.3Hz), 6.87(1H, s),6.93~6.95(2H, m), 7.06(1H, s), 7.09~7.11(2H, m), 7.45(1H, t, J=7.3Hz), 7.51(1H, s). |
| 1BY | H | 1-methylimidazolyl | CH | CH | CH | O | O | 4 | H | H | H | 2 | 1 | 118~121 | (CDCl₃): 4.35(4H, s), 5.06(2H, s),6.89(1H, s), 6.94(2H, d, J=8.8Hz),7.04(2H, d, J=8.8Hz), 7.08(1H, d, J=8.8Hz), 7.19 (1H, s),7.13(2H, d, J=8.8Hz), 7.32(2H, d, J=8.8Hz), 7.53(1H, s), 7.77(1H, s). |

TABLE 13

| | R¹ | R² | X¹ | X² | A | Y | Z | Locant of (CH₂)ₙ | R³ | R⁴ | R⁵ | m | n | m. p. (° C.) | NMR(δ ppm) |
|---|---|---|---|---|---|---|---|---|---|---|---|---|---|---|---|
| 1BZ | H | 3-methylpyridin-yl | N | CH | CH | O | O | 4 | H | H | H | 2 | 1 | 118–120 | (CDCl₃): 4.35(2H, t, J=4.8Hz), 4.73(2H, t, J=4.8Hz), 5.05(2H, s), 6.88~6.96(4H, m), 7.07~7.13(3H, m), 7.36~7.40(1H, m), 7.52(1H, s), 7.79~7.84(2H, m), 8.37(1H, d, J=1.9Hz), 8.61(1H, dd, J=4.8, 1.4Hz), 8.80(1H, d, J=1.9Hz). |
| 1CA | H | 2-methylpyrazin-yl | CH | CH | CH | O | O | 4 | H | H | H | 2 | 1 | 144–146 | (CDCl₃): 4.34~4.41(4H, m), 5.09(2H, s), 6.89(1H, s), 6.94(2H, d, J=8.8Hz), 7.08(1H,s), 7.09(2H, d, J=8.8Hz), 7.13(2H, d, J=8.8Hz), 7.53(1H, s), 7.99(2H, d, J=8.8Hz), 8.45(1H, d, J=2.4Hz), 8.59(1H, dd, J=2.4, 1.5Hz), 8.99(1H, d, J=1.5Hz). |
| 1CB | H | 2,4-difluorophenyl-methyl | N | CH | CH | NCH₃ | O | 4 | H | H | H | 2 | 1 | 96–97 | (CDCl₃): 4.02(2H, t, J=5.3Hz), 4.20(2H, t, J=5.3Hz), 5.02(2H, s), 6.59(2H, d, J=8.7Hz), 6.86~6.94(5H, m), 7.05~7.09(3H, m), 7.32~7.35(1H, m), 7.50(1H, s), 7.63(1H, dt, J=9.0, 1.9Hz), 8.29(1H, s). |
| 1CC | H | benzo[d][1,3]dioxol-yl-methyl | N | CH | CH | O | O | 4 | H | H | H | 2 | 1 | 139–141 | (CDCl₃): 4.34(2H, t, J=4.8Hz), 4.70(2H, t, J=4.8Hz), 5.04(2H, s), 6.00(2H, s), 6.82~6.98(7H, m), 7.06~7.12(3H, m), 7.52(1H,s), 7.72(1H, dd, J=8.7, 2.4Hz), 8.28(1H, d,J=1.9Hz). |
| 1CD | H | 3-methylpyridin-yl | N | CH | CH | O | O | 4 | H | H | H | 2 | 1 | 144–146 | (CDCl₃): 4.34~4.36(2H, m), 4.63~4.74(2H,m), 5.05(2H, s), 6.88~6.95(4H, m), 7.07~7.12(3H, m), 7.45~7.52(2H, m), 7.86(1H,d, J=6.3Hz), 8.45(1H, s), 8.66(2H, d, J=4.8Hz). |
| 1CE | H | 4-hydroxyphenyl-methyl | N | CH | CH | O | O | 4 | H | H | H | 2 | 1 | 200–202 | (DMSO-d₆): 4.31(2H, t, J=4.8Hz), 4.60(2H, t, J=4.8Hz), 5.10(2H, s), 6.83~6.88(4H,m), 6.95~6.97(2H, m), 7.12(1H, s), 7.21(2H, d, J=8.3Hz), 7.44~7.46(2H, m), 7.69(1H,s), 7.90(1H, dd, J=8.3, 2.48Hz), 8.36(1H, d, J=2.9Hz), 9.48(1H, s). |

TABLE 14

| | R[1] | R[2] | X[1] | X[2] | A | Y | Z | Locant of (CH$_2$)$_n$ | R[3] | R[4] | R[5] | m | n | m. p. (° C.) | NMR(δ ppm) |
|---|---|---|---|---|---|---|---|---|---|---|---|---|---|---|---|
| 1CF | H | 4-NH$_2$-phenyl | N | CH | CH | O | O | 4 | H | H | H | 2 | 1 | 184–186 | (CDCl$_3$): 3.75(2H, brs),4.38(2H, t, J=4.8Hz), 4.70(2H,t, J=4.8Hz), 5.04(2H, s), 6.75~6.77 (2H, m), 6.82(1H, d,J=8.7Hz), 6.87(1H, s), 6.92~6.95(2H, m), 7.06~7.12(3H,m), 7.31~7.33(2H, m), 7.52(1H,s), 7.74(1H, dd, J=8.5, 2.4Hz),8.29(1H, d, J=2.4Hz). |
| 1CG | H | 4-SO$_4$ME-phenyl | N | CH | CH | O | O | 4 | H | H | H | 2 | 1 | 163–166 | (CDCl$_3$): 3.09(3H, s), 4.35(2H, t, J=4.8Hz), 4.74(2H, t, J=4.8Hz), 5.05(2H, s), 6.88~6.95 (4H, m), 7.07~7.13(3H, m),7.52(1H, s), 7.70~7.72(2H, m),7.84(1H, dd, J=8.5, 2.4Hz),8.01(2H, d, J=8.3Hz), 8.41(1H,d, J=2.4Hz). |
| 1CH | F | phenyl | CH | CH | CH | O | O | 4 | H | H | H | 2 | 1 | 110–112 | (CDCl$_3$): 4.35~4.37(4H, m),5.06(2H, s), 6.78~6.95(5H, m),7.07~7.14(3H, m), 7.33~7.38 (2H, m),7.52(1H, s),7.83(1H, dd, J=4.8, 1.9Hz),8.57(1H, dd, J=4.8, 1.4Hz),8.75(1H, s). |
| 1CI | H | phenyl | N | N | CH | O | O | 4 | H | H | H | 2 | 1 | amorphous | (CDCl$_3$): 4.36(2H, t, J=4.4Hz),4.78(2H, t, J=4.4Hz), 4.80(2H,s), 6.53(1H, d, J=9.3Hz), 6.81(1H, s), 7.09~7.12(2H,m), 7.19(1H, brs), 7.28~7.32(6H, m), 7.37~7.42(4H, m), 7.51(1H, s), 8.21(1H, s). |
| 1CJ | H | 2,4-diF-phenyl | N | CH | N | O | O | 4 | H | H | H | 2 | 1 | 63–66 (3/2 Fumarate) | (DMSO-d$_6$): 4.26(2H, d, J=4.9Hz), 4.59(2H, d, J=4.9Hz),4.92(2H, s), 6.39(1H, d, J=9.3Hz), 6.63(3H, s), 6.87(1H, d,J=8.3Hz), 6.90(1H, s), 7.13(1H,s), 7.18~7.21(1H, m), 7.33~7.41(2H, m), 7.56~7.62(1H, m), 7.73~7.75(2H, m), 7.87~7.89(1H, m), 8.26(1H, s). |

Test Example 1

Effect of Inhibiting Production of NO and IL-6

Growth of RAW 264.7 cells (mouse macrophage strains) was maintained in an RPMI 1640 medium containing 10% fetal bovine serum (FBS) and an antibiotic (10% FBS/RPMI) under culture conditions of 5% $CO_2$ at 37° C. Upon testing, RAW 264.7 cells were washed with cold Dulbecco's phosphate buffered saline and subsequently removed from the plastic culture bottle by use of EDTA/trypsin. The thus-removed cells were centrifuged-and washed, followed by dilution with 10% FBS/RPMI to $4 \times 10^5$/mL. The cell suspension (0.5 mL) was added to each well of a 24-well-plate, and cultured under 5% $CO_2$, at 37° C. for 16 hours. The percent survival of the cells, as determined through the trypan blue dye exclusion test, was found to be 95% or higher. The live cells were washed once with 1% FBS/RPMI. Each test compound was diluted with the same medium, to thereby adjust the concentration to a predetermined level, and the liquid containing the test compound was added to the washed cells. Two hours after addition, E.-coli-originating lipo-polysaccharide (LPS 026:B6, product of SIGMA) whose concentration had been adjusted to a predetermined level with the medium was added to the cells so as to adjust the final concentration to 25 ng/mL, whereby the cells were stimulated for four hours. After completion of stimulation, the culture suspension containing the test compound and LPS was removed, and the cells were washed twice with the medium. The same medium was added to each well (0.5 mL/well), and culture was further performed for 17 hours. The resultant culture supernatant was stored at −20° C. until analysis of the supernatant. In each case, the test was repeated three times. NO contained in the culture supernatant was quantitated for its stable form ($NO_2^-$) by use of a Griess reagent kit (product of Wako Pure Chemical Industries Ltd.). IL-6 was quantitated by use of an ELISA kit (product of Amersham) in accordance with the manual thereof. Percent inhibition of production of NO and IL-6 caused by the test compound was calculated in accordance with the following equation:

Percent inhibition (%)=[(control−production in the presence of test compound)/(control)]×100;

wherein the amount of produced NO or IL-6 in the absence of the test compound was postulated to be 100%. The results are shown in Tables 15 to 17.

TABLE 15

| Compounds of the invention | NO production inhibitory effect Percent inhibition (%) |
|---|---|
| (2 μg/mL) | |
| 1A | 86.0 |
| 1C | 83.5 |
| 1H | 83.5 |
| 1I | 62.8 |
| 1K | 61.2 |
| 1M | 82.6 |

TABLE 16

| Compounds of the invention (0.02 μg/mL) | NO production inhibitory effect Percent inhibition (%) |
|---|---|
| 1Z | 68.5 |
| 1AA | 76.0 |
| 1AL | 96.1 |
| 1AX | 60.4 |
| 1AY | 93.9 |
| 1BJ | 51.3 |
| 1BL | 49.6 |
| 1BO | 54.2 |
| 1BP | 57.3 |
| 1BR | 91.6 |
| 1BT | 59.7 |
| 1BU | 98.0 |

TABLE 17

| Compounds of the invention (2 μg/mL) | IL-6 production inhibitory effect Percent inhibition (%) |
|---|---|
| 1A | 54.6 |
| 1C | 49.7 |
| 1H | 65.2 |
| 1T | 77.9 |
| 1K | 58.2 |
| 1M | 51.7 |

The results shown in these Tables indicate that the compounds of the present invention exert an excellent effect of inhibiting production of NO and IL-6.

Test Example 2

Anti-inflammatory Effect 1: Effect Against Carrageenan-induced Edema (1) Test Animal:

Male ICR mice (4 weeks old, Japan Charles River Co., Ltd.) were pre-bred in a breeding cage for about one week, and-healthy mice were selected for the test.

(2) Drugs Employed in the Test:

Each test compound was suspended in a 0.5% carboxymethyl cellulose sodium (0.5% CMC-Na solution, product of Wako Pure Chemical Industries, Ltd.) or dissolved in purified water. The suspension or solution was perorally administered at a dose of 0.1 mL/10 g (body weight of each mouse).

λ-Carrageenan (Picnin A, product of Zushi Kagaku) dissolved in physiological saline was used.

(3) Test Method:

The volume of the right rear leg of each mouse was measured by means of a plethysmometer (product of Ugo Basile). Subsequently, a 2% carrageenan solution (0.05 mL) was injected into the foot pad of the leg. Five days after the injection of carrageenan (inflammation-inducing agent), the volume of the leg was measured. The mice were divided into groups, each group containing 8 mice. From the day of division (i.e., 5 days after administration of carrageenan), each test compound was preorally administered once per day for four days. The leg volume was measured before administration of each test compound and on the day after the final administration day (i.e., 9 days after administration of carrageenan). Percent edema and percent inhibition due to the test compound were calculated in accordance with the following equations, respectively. The results are shown in Table 18.

Percent edema (%)=[(leg volume (mL) after inflammation treatment−leg volume (mL) before inflammation treatment)/(leg volume (mL) before inflammation treatment)]×100

Percent inhibition (%)=[percent edema of control group (%)−percent edema of test-compound-administered group (%))/(percent edema of control group (%))]×100

TABLE 18

| Compounds | Amount of administration (mg/kg) | Percent inhibition (%) | Compounds | Amount of administration (mg/kg) | Percent inhibition (%) |
|---|---|---|---|---|---|
| 1A | 3 | 30.5 | 1AL | 10 | 27.6 |
| 1C | 10 | 31.8 | 1AY | 10 | 23.0 |
| 1D | 10 | 28.6 | 1BJ | 10 | 38.8 |
| 1J | 10 | 41.2 | 1BP | 10 | 26.4 |
| 1K | 10 | 42.7 | 1BR | 10 | 24.9 |
| 1AT | 10 | 20.8 | Indomethacin | 1 | 23.8 |

The results shown in Table 18 indicate that the compounds of the present invention exert an excellent anti-inflammatory effect.

Test Example 3

Anti-inflammatory Effect 2: Effect of Treating Collagen Arthritis (1) Drugs Employed in the Test:

Type II collagen (originating from cattle joints) was dissolved in a 0.05M acetic acid solution, and the resultant solution was mixed with complete Freund's adjuvant at 1:1, to thereby yield an emulsion having a collagen content of 1 mg/mL.

(2) Test Method:

DBA/1J mice (Japan Charles River Co., Ltd.) were immunized with type II collagen (0.1 mg/body). Twenty-one days after immunization, the animals were boosted with same amount of type II collagen. Seven days after boosting, the inflammation score of the limbs of each mouse was evaluated. The mice were divided into groups, each group containing 7 mice, such that the inflammation score of the control group and that of Compound-(1A)-administered group were virtually equal to each other. Each leg was evaluated in terms of degree of inflammation, with most severe conditions being rated at a score of 3 and (0: no change, 1: slight edema, 2: medium edema, 3: severe edema with joint agglutination, with a minimum unit of 0.5). The inflammation score was expressed as the sum of the scores of four limbs. The Compound (1A) of the present invention (0.5% CMC-Na solution) was perorally administered once per day at a dose of 30 mg/kg/day for 23 days from the day of grouping.

The results are shown in FIG. 1. As is clear from FIG. 1, the compounds of the present invention exert an excellent anti-inflammatory effect also on model chronic inflammation and are useful as drugs for treating inflammatory diseases such as rheumatoid arthritis.

Industrial Applicability

The imidazole derivatives (1) or salts thereof of the present invention exert excellent effects of inhibiting production of NO and IL-6 and are useful for preventing or treating diseases induced by overproduction of NO and IL-6.

What is claimed is:

1. An imidazole derivative represented by formula (1), or a salt thereof:

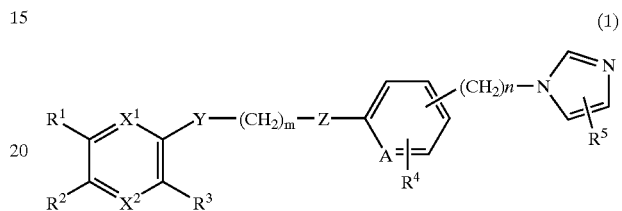

(1)

wherein each of $R^1$ and $R^2$, independently represents a hydrogen atom, an alkyl group, a halogen atom, an aryl group which may be substituted, or a heteroaryl group which may be substituted;

(1) A represents N or CH, and one of $X^1$ and $X^2$ represents N, the other represents CH, or (2) A represents N, and $X^1$ and $X^2$ each represents CH;

each of Y and Z, independently represents O, S, SO, $SO_2$, $CH_2$, NH, or N—$R^6$, wherein $R^6$ represents an alkyl group, an aryl group which may be substituted, or a heteroaryl group which may be substituted;

each of $R^3$, $R^4$, and $R^5$, independently represents a hydrogen atom, an alkyl group, an alkoxy group, a halogen atom, a halogenoalkyl group, a nitro group, an amino group, a hydroxyl group, a cyano group, an acyl group, a carboxyl group, a carbamoyl group, a substituted amide group, a substituted sulfonamido group, or a phenyl group which may be substituted;

m is a number of 1 to 4;

and n is a number of 0 to 4.

2. The imidazole derivative, or a salt thereof, according to claim 1, wherein each of $R^1$ and $R^2$, independently represents a hydrogen atom; an alkyl group; a halogen atom; a C6–C14 aryl group, which may have one to three substituents selected from the group consisting of a halogen atom, a nitro group, an amino group, an alkyl group, a hydroxyl group, an alkoxy group, an alkylthio group, an alkylsulfonyl group, an alkylenedioxy group, and a halogenoalkyl group; or a 5- or 6-membered heteroaryl group which has one or two atoms of nitrogen, sulfur, or oxygen, and which may have one to three substituents selected from the group consisting of a halogen atom, a nitro group, an amino group, an alkyl group, a hydroxyl group, an alkoxy group, an alkylthio group, an alkylsulfonyl group, an alkylenedioxy group, and a halogenoalkyl group;

(1) A represents N or CH, and one of $X^1$ and $X^2$ represents N, the other represents CH, or (2) A represents N, and $X^1$ and $X^2$ each represents CH;

each of Y and Z, independently represents O, S, SO, $SO_2$, $CH_2$, NH or N—$R^6$, wherein $R^6$ represents an alkyl group; a C6–C14 aryl group, which maybe substituted by an alkyl group, an alkoxy group, an amino group, or a sulfonamide group; or a 5- or 6-membered heteroaryl group, which has one or two atoms of nitrogen, sulfur, or oxygen, and which may be substituted by an alkyl group, an alkoxy group, an amino group, or a sulfonamide group;

each of $R^3$, $R^4$, and $R^5$, independently represents a hydrogen atom, an alkyl group, an alkoxy group, a halogen atom, a halogenoalkyl group, a nitro group, an amino group, a hydroxyl group, a cyano group, an alkanoyl group, a carboxyl group, a carbamoyl group, an alkanoylamino group, an alkanesulfonamido group, or a phenyl group, which may be substituted by an alkyl group, an alkoxy group, an amino group, or a sulfonamido group;

m is a number of 1 to 4; and n is a number of 0 to 4.

3. A composition, comprising, as an active ingredient, the imidazole derivative, or a salt thereof, according to claim 1, and one or more additives.

4. A composition comprising, the imidazole derivative, or a salt thereof, according to claim 1, and a pharmaceutically acceptable carrier.

5. A method of producing a drug, comprising contacting the imidazole derivative, or a salt thereof, according to claim 1, with one or more pharmaceutically acceptable additives.

6. A composition, comprising, as an active ingredient, an effective amount of the imidazole derivative, or a salt thereof, according to claim 2, and one or more additives.

7. A composition, comprising the imidazole derivative, or a salt thereof, according to claim 2, and a pharmaceutically acceptable carrier.

8. A method of producing a drug, comprising, contacting the imidazole derivative, or a salt thereof, according to claim 2, with one or more pharmaceutically acceptable additives.

9. A method of inhibiting the production of nitric oxide and/or IL-6, comprising, administering to a subject in need thereof, an effective amount of the imidazole derivative, or a salt thereof, according to claim 1.

10. A method of inhibiting the production of nitric oxide and/or IL-6, comprising, administering to a subject in need thereof, an effective amount of the imidazole derivative, or a salt thereof, as recited in claim 2.

11. A method of treating rheumatoid arthritis, comprising, administering to a subject in need thereof, an effective amount of the imidazole derivative, or a salt thereof, according to claim 1.

12. A method of treating rheumatoid arthritis, comprising, administering to a subject in need thereof, an effective amount of the imidazole derivative, or a salt thereof, according to claim 2.

13. A method of reducing edema, comprising, administering to a subject in need thereof, an effective amount of the imidazole derivative, or a salt thereof, according to claim 1.

14. A method of reducing edema, comprising, administering to a subject in need thereof, an effective amount of the imidazole derivative, or a salt thereof, according to claim 2.

15. The method of claim 9, wherein the imidazole derivative, or a salt thereof, is administered at 0.1 to 1,000 mg per day.

16. The method of claim 9, wherein the subject in need is a human or other mammal.

17. The method of claim 11, wherein the imidazole derivative, or a salt thereof, is administered at 0.1 to 1,000 mg per day.

18. The method of claim 11, wherein the subject in need is a human or other mammal.

19. The method of claim 13, wherein the imidazole derivative, or a salt thereof, is administered at 0.1 to 1,000 mg per day.

20. The method of claim 13, wherein the subject in need is a human or other mammal.

* * * * *